(12) United States Patent
Weeber

(10) Patent No.: US 8,231,219 B2
(45) Date of Patent: Jul. 31, 2012

(54) DIFFRACTIVE LENS EXHIBITING ENHANCED OPTICAL PERFORMANCE

(75) Inventor: Hendrik A. Weeber, Groningen (NL)

(73) Assignee: AMO Groningen B.V., Santa Ana, CA (US)

( * ) Notice: Subject to any disclaimer, the term of this patent is extended or adjusted under 35 U.S.C. 154(b) by 236 days.

(21) Appl. No.: 12/429,155

(22) Filed: Apr. 23, 2009

(65) Prior Publication Data

US 2009/0268155 A1  Oct. 29, 2009

Related U.S. Application Data

(63) Continuation-in-part of application No. 12/109,251, filed on Apr. 24, 2008, now Pat. No. 7,871,162.

(60) Provisional application No. 61/047,699, filed on Apr. 24, 2008.

(51) Int. Cl.
*G02C 7/06* (2006.01)
(52) U.S. Cl. ......... 351/168; 359/558; 359/571; 351/159
(58) Field of Classification Search .......... 351/168–172, 351/159.44; 359/558, 571
See application file for complete search history.

(56) References Cited

U.S. PATENT DOCUMENTS

| | | |
|---|---|---|
| 3,367,734 A | 2/1968 | Bystricky et al. |
| 4,637,697 A | 1/1987 | Freeman |
| 4,642,112 A | 2/1987 | Freeman |
| 4,655,565 A | 4/1987 | Freeman |
| 4,778,462 A | 10/1988 | Grendahl |
| 4,795,462 A | 1/1989 | Grendahl |
| 4,798,608 A | 1/1989 | Grendahl |
| 4,798,609 A | 1/1989 | Grendahl |
| 4,932,970 A | 6/1990 | Portney |
| 4,995,714 A | 2/1991 | Cohen |
| 5,016,977 A | 5/1991 | Baude et al. |
| 5,056,908 A | 10/1991 | Cohen |
| 5,066,301 A | 11/1991 | Wiley |
| 5,089,023 A | 2/1992 | Swanson |
| 5,096,285 A | 3/1992 | Silberman |
| 5,114,220 A | 5/1992 | Baude et al. |
| 5,117,306 A | 5/1992 | Cohen |

(Continued)

FOREIGN PATENT DOCUMENTS

EP   0 343 067 A1   11/1989

(Continued)

OTHER PUBLICATIONS van den Berg, T. J. "Analysis of Intraocular Straylight, Especially in Relation to Age" Optom. Vis. Sci., 1995 72(2) pp. 52-59.

(Continued)

*Primary Examiner* — Jessica T Stultz
(74) *Attorney, Agent, or Firm* — AMO Groningen B.V.

(57) ABSTRACT

The present invention provides improved ophthalmic lenses and methods for their design and use. Monofocal and multifocal diffractive ophthalmic lenses having reduced light scatter, improved light energy distribution properties, and/or other improvements in optical performance are provided. These properties are provided, at least in part, by the diffractive profiles of the invention, often having subtlety shaped echelettes with appropriately curving profiles. Smooth diffractive profiles may be used reduce light scatter. Diffractive profiles may be configured to limit the light energy in certain selected orders, thereby improving viewing quality and mitigating unwanted effects such as dysphotopsia. Diffractive profiles of may additionally or alternatively vary the light energy distributed between individual echelettes, providing additional advantages in various viewing situations.

4 Claims, 12 Drawing Sheets

U.S. PATENT DOCUMENTS

| | | | |
|---|---|---|---|
| 5,120,120 A | 6/1992 | Cohen | |
| 5,121,979 A | 6/1992 | Cohen | |
| 5,121,980 A | 6/1992 | Cohen | |
| 5,144,483 A | 9/1992 | Cohen | |
| 5,225,858 A | 7/1993 | Portney | |
| 5,229,797 A | 7/1993 | Futhey et al. | |
| 5,652,638 A | 7/1997 | Roffman et al. | |
| 5,699,142 A | 12/1997 | Lee et al. | |
| 5,748,282 A | 5/1998 | Freeman | |
| 5,760,871 A * | 6/1998 | Kosoburd et al. | 623/6.3 |
| 5,796,462 A | 8/1998 | Roffman et al. | |
| 5,968,094 A | 10/1999 | Werblin et al. | |
| 6,126,283 A | 10/2000 | Wen et al. | |
| 6,126,286 A | 10/2000 | Portney | |
| 6,142,625 A | 11/2000 | Sawano et al. | |
| 6,210,005 B1 | 4/2001 | Portney | |
| 6,338,559 B1 | 1/2002 | Williams et al. | |
| 6,457,826 B1 | 10/2002 | Lett | |
| 6,464,355 B1 | 10/2002 | Gil | |
| 6,474,814 B1 | 11/2002 | Griffin | |
| 6,488,708 B2 | 12/2002 | Sarfarazi | |
| 6,491,721 B2 | 12/2002 | Freeman et al. | |
| 6,527,389 B2 | 3/2003 | Portney | |
| 6,533,416 B1 | 3/2003 | Fermigier et al. | |
| 6,536,899 B1 | 3/2003 | Fiala | |
| 6,537,317 B1 | 3/2003 | Steinert et al. | |
| 6,547,822 B1 | 4/2003 | Lang | |
| 6,554,859 B1 | 4/2003 | Lang et al. | |
| 6,557,992 B1 | 5/2003 | Dwyer et al. | |
| 6,609,793 B2 | 8/2003 | Norrby et al. | |
| 6,705,729 B2 | 3/2004 | Piers et al. | |
| 6,808,262 B2 | 10/2004 | Chapoy et al. | |
| 6,830,332 B2 | 12/2004 | Piers et al. | |
| 6,846,326 B2 | 1/2005 | Zadno-Azizi et al. | |
| 6,851,803 B2 | 2/2005 | Wooley et al. | |
| 6,923,539 B2 | 8/2005 | Simpson et al. | |
| 6,923,540 B2 | 8/2005 | Ye et al. | |
| 6,986,578 B2 | 1/2006 | Jones | |
| 7,036,931 B2 | 5/2006 | Lindacher et al. | |
| 7,048,760 B2 | 5/2006 | Cumming | |
| 7,061,693 B2 | 6/2006 | Zalevsky | |
| 7,073,906 B1 * | 7/2006 | Portney | 351/168 |
| 7,137,702 B2 | 11/2006 | Piers et al. | |
| 7,156,516 B2 | 1/2007 | Morris et al. | |
| 7,188,949 B2 | 3/2007 | Bandhauer et al. | |
| 7,287,852 B2 | 10/2007 | Fiala | |
| 7,293,873 B2 | 11/2007 | Dai et al. | |
| 7,365,917 B2 | 4/2008 | Zalevsky | |
| 7,377,640 B2 | 5/2008 | Piers et al. | |
| 7,441,894 B2 | 10/2008 | Zhang et al. | |
| 7,475,986 B2 | 1/2009 | Dai et al. | |
| 7,615,073 B2 | 11/2009 | Deacon et al. | |
| 7,871,162 B2 | 1/2011 | Weeber | |
| 2002/0118337 A1 | 8/2002 | Perrott et al. | |
| 2003/0076478 A1 | 4/2003 | Cox | |
| 2003/0171808 A1 | 9/2003 | Phillips | |
| 2004/0021824 A1 | 2/2004 | Ye et al. | |
| 2004/0085515 A1 | 5/2004 | Roffman et al. | |
| 2004/0106992 A1 | 6/2004 | Lang et al. | |
| 2004/0111153 A1 | 6/2004 | Woods et al. | |
| 2004/0150789 A1 | 8/2004 | Jones | |
| 2004/0156014 A1 | 8/2004 | Piers et al. | |
| 2004/0230299 A1 | 11/2004 | Simpson et al. | |
| 2005/0096226 A1 | 5/2005 | Stock et al. | |
| 2005/0128432 A1 | 6/2005 | Altmann | |
| 2005/0203619 A1 | 9/2005 | Altmann | |
| 2005/0267575 A1 | 12/2005 | Nguyen et al. | |
| 2006/0009816 A1 | 1/2006 | Fang et al. | |
| 2006/0030938 A1 | 2/2006 | Altmann | |
| 2006/0034003 A1 | 2/2006 | Zalevsky | |
| 2006/0055883 A1 * | 3/2006 | Morris et al. | 351/168 |
| 2006/0066808 A1 | 3/2006 | Blum et al. | |
| 2006/0098162 A1 | 5/2006 | Bandhauer et al. | |
| 2006/0098163 A1 | 5/2006 | Bandhauer et al. | |
| 2006/0109421 A1 | 5/2006 | Ye et al. | |
| 2006/0116763 A1 | 6/2006 | Simpson | |
| 2006/0116764 A1 | 6/2006 | Simpson | |
| 2006/0176572 A1 | 8/2006 | Fiala | |
| 2006/0238702 A1 | 10/2006 | Glick et al. | |
| 2006/0244904 A1 | 11/2006 | Hong et al. | |
| 2007/0052920 A1 | 3/2007 | Stewart et al. | |
| 2007/0129803 A1 | 6/2007 | Cumming et al. | |
| 2007/0171362 A1 | 7/2007 | Simpson et al. | |
| 2007/0182924 A1 | 8/2007 | Hong et al. | |
| 2008/0030677 A1 | 2/2008 | Simpson | |
| 2008/0161913 A1 | 7/2008 | Brady et al. | |
| 2008/0161914 A1 | 7/2008 | Brady et al. | |
| 2009/0062911 A1 | 3/2009 | Bogaert | |
| 2009/0164008 A1 | 6/2009 | Hong et al. | |
| 2009/0187242 A1 | 7/2009 | Weeber et al. | |
| 2009/0210054 A1 | 8/2009 | Weeber et al. | |
| 2009/0234448 A1 | 9/2009 | Weeber et al. | |
| 2009/0268158 A1 | 10/2009 | Weeber | |
| 2009/0295295 A1 | 12/2009 | Shannon et al. | |
| 2009/0323020 A1 | 12/2009 | Zhao et al. | |
| 2010/0161048 A1 | 6/2010 | Schaper, Jr. | |

FOREIGN PATENT DOCUMENTS

| | | |
|---|---|---|
| EP | 457553 A2 | 11/1991 |
| EP | 0 681 198 A1 | 11/1995 |
| EP | 0926531 A1 | 6/1999 |
| EP | 949529 A2 | 10/1999 |
| EP | 1424049 A1 | 6/2004 |
| EP | 1310267 B1 | 1/2008 |
| EP | 1424049 B1 | 6/2009 |
| WO | WO9222264 A1 | 12/1992 |
| WO | WO9303409 A1 | 2/1993 |
| WO | WO0019906 A1 | 4/2000 |
| WO | WO0163344 A1 | 8/2001 |
| WO | WO0182839 A1 | 11/2001 |
| WO | WO0189424 A1 | 11/2001 |
| WO | WO0221194 A2 | 3/2002 |
| WO | WO03009053 A1 | 1/2003 |
| WO | WO2004034129 A1 | 4/2004 |
| WO | WO2004090611 A2 | 10/2004 |
| WO | WO2004096014 A2 | 11/2004 |
| WO | WO2005019906 A1 | 3/2005 |
| WO | WO2006025726 A1 | 3/2006 |
| WO | WO2006047698 A1 | 5/2006 |
| WO | 2006/060480 A2 | 6/2006 |
| WO | WO2006060477 A2 | 6/2006 |
| WO | 2007/092948 A1 | 8/2007 |
| WO | WO2007133384 A2 | 11/2007 |
| WO | WO2008045847 A2 | 4/2008 |
| WO | WO2009076670 A1 | 6/2009 |

OTHER PUBLICATIONS

Alfonso et al. "Prospective study of the Acri.LISA bifocal Intraocular Lens" J Cataract Refract Surg. vol. 33, Nov. 2007 pp. 1930-1935.

Siedlecki et al. "Radial gradient index intraocular lens: a theoretical model" Journal of Modern Optics, vol. 55, Nos. 4-5 Feb. 20-Mar. 10, 2008, pp. 639-647.

U.S. Appl. No. 12/109,251, filed Apr. 24, 2008.

Canovas C., et al., "Hybrid Adaptive-Optics Visual Simulator," Optical Letters, 2010, vol. 35 (2), pp. 196-198.

Cohen, Allen L., "Practical design of a bifocal hologram contact lens or intraocular lens," Applied Optics, 1992, 31 (19), 3750-3754.

Diffractive Lenses for Extended Depth of Focus and Presbyopic Correction. Presentation from Wavefront Congress held on Feb. 15, 2008, Rochester, New York.

Doskolovich L.L., et al., "Special Diffractive Lenses," SPIE, 1992, vol. 1780, pp. 393-402.

International Search Report for Application No. PCT/EP2009/051783, mailed on Apr. 28, 2009, 3 pages.

International Search Report for Application No. PCT/US09/042449, mailed on Nov. 5, 2009, 5 pages.

International Search Report for Application No. PCT/US2010/038167, mailed on Sep. 27, 2010, 2 pages.

Liou H.L., et al., "Anatomically Accurate, Finite Model Eye for Optical Modeling," Journal of Optical Society of America, 1997, vol. 14 (8), pp. 1684-1695.

Marsack J.D., et al., "Metrics of Optical Quality Derived From Wave Aberrations Predict Visual Performance," Journal of Vision, 2004, vol. 4 (4), pp. 322-328.

Monsoriu J.A., et al., "Devil's Lenses," Optics Express, 2007, vol. 15 (21), pp. 13858-13864.
Norrby S., et al., "Model Eyes for Evaluation of Intraocular Lenses," Applied Optics, 2007, vol. 46 (26), pp. 6595-6605.
Piers P.A., et al., "Theoretical Comparison of Aberration-Correcting Customized and Aspheric Intraocular Lenses," Journal of Refractive Surgery, 2007, vol. 23 (4), pp. 374-384.
Van Meeteren A., "Calculations on the Optical Modulation Transfer Function of the Human Eye for White Light," Optica Acta, 1974, vol. 21 (5), pp. 395-412.
Villegas E.A., et al., "Correlation between Optical and Psychophy, Sical Parameters as a Function of Defocus," Optometry and Vision Science, 2002, vol. 79 (1), pp. 60-67.
International Search Report and Written Opinion for Application No. PCT/IB2011/001067, mailed on Sep. 13, 2011, 13 pages.
Piers P.A., et al., "Eye Models for the Prediction of Contrast Vision in Patients with New Intraocular Lens Designs," Optics Letters, 2004, vol. 29 (7), pp. 733-735.

Terwee T., et al., "Visualization of the Retinal Image in an Eye Model With Spherical and Aspheric, Diffractive, and Refractive Multifocal Intraocular Lenses," Journal of Refractive Surgery, 2008, vol. 24 (3), pp. 223-232.
Co-pending U.S. Appl. No. 12/771,550, filed Apr. 30. 2010.
International Search Report for Application No. PCT/IB2009/005590, mailed on Sep. 30, 2009, 3 pages
International Search Report for Application No. PCT/US08/073999, mailed on Dec. 3, 2008, 3 pages.
International Search Report for Application No. PCT/US2010/061081, mailed on Apr. 6, 2011, 2 pages.
U.S. Appl. No. 12/129,155, filed May 29, 2008.
U.S. Appl. No. 11/618,325, filed Dec. 29, 2006 (Brady et al).
U.S. Appl. No. 11/618,411, filed Dec. 29, 2006(Bradyetai).

* cited by examiner

--Prior Art--

--Prior Art--

$$\Delta(\rho) := \Delta_0 \cdot \left[ \left[ \left[ 1 - \left( \frac{\rho}{r_1^2} \right) \right]^{en} \cdot \left[ 1 - \left( \frac{\rho}{r_1^2} \right) \right] \right] + \left[ \left( \left( \frac{\rho}{r_1^2} \right) \right)^{en} \right] \right] \cdot \left[ 0.5 + 0.5 \cos \left[ \pi \frac{\rho}{q_1^2} \left[ 1.0 + \left( \rho - q_1^2 \right) \right] \right] \right] \cdot \left[ Y\_min + (Y\_max - Y\_min) \cdot \left[ 0.5 \tanh \left[ \frac{(\rho - X\_shift)}{m} \right] + 0.5 \right] \right]$$

FIG. 4E

DIFFRACTIVE LENS EXHIBITING ENHANCED OPTICAL PERFORMANCE

CROSS-REFERENCES TO RELATED APPLICATIONS

The present application is a continuation-in-part application of, and claims prior to, U.S. patent application Ser. No. 12/109,251, filed Apr. 24, 2008 and also claims priority under 35 U.S.C. §119(e) to provisional application No. 61/047,699, filed on Apr. 24, 2008, the entire contents of each of which applications are hereby incorporated by reference in their entirety for all purposes as if fully set forth herein.

BACKGROUND OF THE INVENTION

1. Field of the Invention

The present invention relates to ophthalmic lenses such as, for example, contact lenses or intraocular lenses (IOLs). Exemplary embodiments include monofocal and multifocal diffractive ophthalmic lenses having reduced light scatter and/or improved light energy distribution, for example through subtle shaping of echelettes with appropriately curving profiles.

2. Description of Background Art

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages, and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only limited ability to change shape.

Along with reductions in accommodation of the eye, age may also induce clouding of the lens due to the formation of cataracts. Cataracts may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intraocular lens or "IOL".

A variety of technologies have been developed to enhance the ability of IOLs to facilitate viewing. Multifocal IOLs may, for example, often rely on a diffractive optical surface to direct portions of the light energy toward differing focal distances, thereby allowing the patient to clearly see both near and far objects. Alternative diffractive multifocal ophthalmic lenses (including contact lenses or the like) have been proposed for treatments of presbyopia without removal of the natural crystalline lens. Diffractive optical surfaces, either monofocal or multifocal, may also be configured to provide reduced chromatic aberrations.

Like other lenses, diffractive monofocal and multifocal lenses can make use of a material having a given refractive index and a surface curvature to provide a refractive power. Diffractive lenses also have a diffractive profile which confers the lens with a diffractive power that contributes to the overall optical power of the lens. The diffractive profile is typically characterized by a number of diffractive zones. The diffractive power is related to the properties of these zones, for instance their number, shape, size and position. When used for ophthalmic lenses these zones are typically annular lens zones, or echelettes, spaced about the optical axis of the lens. Currently used echelettes may typically be defined by a primary zone, a secondary zone between the primary zone and a primary zone of an adjacent echelette, and an echelette geometry. The echelette geometry includes limiting inner and outer diameters and a shaped or sloped profile. Secondary zones may describe the situation where the theoretical primary zone is a discontinuous function, leading to discrete steps in the profile height. Secondary zones may be introduced to solve the manufacturing issue of making sharp corner in a surface, and/or to reduce possible light scatter from sharp corners. The overall profile may be characterized by an echelette height or step height between adjacent echelettes. The relative radial spacing of the echelettes largely determine the power(s) of the lens and the step height of the secondary zones largely determines the light distribution between the different add powers. Together, these echelettes define a diffractive profile, often saw-toothed or stepped, on one of the surfaces of the lens.

A multifocal diffractive profile of the lens can be used to mitigate presbyopia by providing two or more optical powers, for example, one for near vision and one for far vision. These lenses may be in the form of a multifocal contact lens, most commonly a bifocal contact lens. The lenses may also take the form of an intraocular lens placed within the capsular bag of the eye, replacing the original lens.

Although monofocal and multifocal diffractive ophthalmic lenses have greatly improved the quality of vision for many patients, additional improvements would still be beneficial. For example, some pseudophakic patients may experience effects such as halos and scatter. Therefore, monofocal and multifocal diffractive lenses having diffractive profiles resulting in reduced scatter (and thus an improved quality of vision) may be beneficial. For multifocal lenses, along with directing portions of the incident light energy at focal distances suitable for near and far viewing, diffractive optics may also direct significant light energy at other non-viewing foci, which can contribute to unwanted light-related visual phenomenon experienced by the patient (dysphotopsia). Having non-viewing foci of diffractive optics of multifocal lenses cannot be completely avoided. However, diffractive multifocal lenses having diffractive profiles which optimize the light energy distribution between viewing and non-viewing foci to improve quality of vision would also be beneficial. Controllably varying light distributions over the diffractive profile may also provide advantages, so that diffractive multifocal lenses having diffractive profiles which vary light distribution over the profile may be desirable.

BRIEF SUMMARY OF THE INVENTION

The present invention generally provides improved lenses and imaging techniques. Embodiments of the present invention provide improved ophthalmic lenses (including, for example contact lenses, intraocular lenses (IOLs), and the like) and associated methods for their design and use. Exemplary embodiments provide monofocal and/or multifocal diffractive ophthalmic lenses having reduced light scatter and/or improved light energy distribution, for example, through subtle shaping of echelettes with appropriately curving profiles extending between primary zones of adjacent secondary zones. In some embodiments, diffractive ophthalmic lenses having multiple foci use a zero (or alternatively a first) diffractive order for far vision and a first (or alternatively a second) diffractive order for near vision, while limiting the light energy directed to other unwanted diffractive orders or non-viewing diffractive orders. Advantageously, it has been recognized that light energy to foci of a selected subset of these non-viewing diffractive orders—specifically, those that are closest to the zero order focus—can have an disproportionate effect on vision quality. By limiting the light energy in such selected orders (optionally, even at the cost of directing more total light energy to other higher and/or non-viewing diffractive orders or foci), dysphotopsia may be mitigated. Imposing a controlled continuously curved profile across a series of echelettes can be used to tailor energies of the various foci or diffractive orders so as to provide such benefits, and/or may be used to limit scatter effects which may otherwise be generated by conventional diffractive echelettes.

In a first aspect, the invention provides a multifocal ophthalmic lens. The provide lens includes an anterior face and a posterior face. Each face has a corresponding refractive profile. The faces are disposed about an optical axis. The faces may often define a clear aperture. The multifocal ophthalmic lens also includes a diffractive profile imposed on one of the refractive profiles. The diffractive profile is characterized by a continuous function over a plurality of echelettes. In the visible waveband, the diffractive profile has a zeroth diffractive order, a first diffractive order having a diffraction add power and a minus one diffractive order. The minus one diffractive order has a lower diffractive efficiency than a reference lens having the same anterior face, posterior face, and diffraction add power.

In many embodiments, the light energy distribution between the zeroth and the first diffractive order is between 80%:20% and 40%:60%. In some embodiments, the distribution is approximately 50%:50%.

In many embodiments, the diffraction efficiency of the minus one diffractive order is less than about 4 percent. In some embodiments, the diffraction efficiency of the minus one diffractive order is less than 2.5 percent.

In another aspect, the invention provides a diffractive ophthalmic lens including an anterior face and a posterior face. Each face has a refractive profile. The faces are disposed about an optical axis and define a clear aperture. A diffractive profile is imposed on one of the refractive profiles. The diffractive profile is characterized by a continuous function over a plurality of echelettes, the continuous function comprising a power function and a stretch function. The provided diffractive ophthalmic lens may be monofocal, bifocal, or multifocal.

In some embodiments, the continuous function is described by the equation shown in FIG. 4C over a plurality of echelettes including a first or central echelette and a plurality of surrounding echelettes, where $\rho$ is the square of a radial distance from the optical axis, en is an exponential power; $r_1$ is a radius of the central echelette, $q_1$ affects the size of a primary zone of each echelette, so that $r_1-q_1$ affects the size of a secondary zone of each echelette; Y_min and m are parameters influencing the shape of the echelette; Y_max is $(2q_1^2-r_1^2)/(r_1^2-q_1^2)/r_1^2$; X_shift is $q_1^2$; and $\Delta\rho$ is the height of the profile. The primary and secondary zones combine to provide a smooth continuous surface, generally free from discontinuities. In some embodiments, the primary zone is characterized by a decreasing zone height with increasing $\rho$, while the secondary zone is characterized by increasing zone height with increasing $\rho$.

In another aspect, the invention provides a diffractive ophthalmic lens for use with an eye of a patient. The diffractive ophthalmic lens includes a diffractive surface. An optical axis extends through the diffractive surface. The diffractive surface has a plurality of echelettes. When viewing along the optical axis of the eye, the echelettes provide at least one viewing diffractive order. The at least one viewing diffractive order each has an associated viewing focus for viewing at a distance from the eye. The echelettes have sufficiently smooth curving profiles throughout the diffractive surface to inhibit step-induced scatter. The provided diffractive ophthalmic lens may be monofocal, bifocal, or multifocal.

In certain embodiments, the echelette also includes an echelette geometry which includes an overall shape and a height of the along the optical axis. The spacing of the echelettes defines the at least one viewing focus. The echelette geometry defines a smooth profile that inhibits scatter such that the scatter from the lens is lower than the scatter of a reference diffractive lens having the same spacing between corresponding echelettes, an echelette geometry that is parabolic, and an axial step between adjacent echelettes. In some embodiments, the scatter of the lens, as defined by a stray light parameter, is at least 25% lower than the scatter of the diffractive reference lens.

In certain embodiments, for the entire zone profile, the local radii of curvature are greater than the wavelength of incoming visible light. In some embodiments, the slopes of the primary zone functions and the slopes of the adjacent secondary zone functions are substantially equal. The primary zone functions are curved throughout a significant portion of the primary zones when axial height of the diffractive surface is plotted as a function of a radius squared from the optical axis. In some embodiments, the primary zone function comprises a cosine function raised per a power function and shifted by a stretch function.

In many embodiments, the at least one viewing focus includes a zero diffractive order focus and a first diffractive order focus. The zero diffractive order focus provides viewing at a far viewing distance from the eye. The first diffractive order focus provides viewing at a near viewing distance from the eye. More than 75% of incoming visible light energy is directed to the at least one viewing focus. In other embodiments, the at least one viewing focus includes a first diffractive order focus and a second diffractive order focus. In such embodiments, the first diffractive order focus provides viewing at a far viewing distance from the eye and the second diffractive order focus provides viewing at a near viewing distance from the eye.

In another aspect, the invention provides a method for enhancing viewing satisfaction of a diffractive ophthalmic lens for use with an eye of a person. The ophthalmic lens includes a diffractive surface with a plurality of echelettes. When viewing along the optical axis with the eye, the echelettes provide at least one viewing diffractive order. The at least one diffractive viewing diffractive order each has an associated viewing focus for viewing at a distance from the eye. The method includes smoothly curving the echelette profiles across the diffractive surface sufficiently to inhibit step-induced scatter. The diffractive ophthalmic lens may be monofocal, bifocal, or multifocal.

In another aspect, the invention provides a diffractive ophthalmic lens for use with an eye of a person having a retina. The ophthalmic lens includes an anterior face and an opposing posterior face disposed about an optical axis. The faces define a clear aperture with a refractive optical power. The ophthalmic lens also includes a diffractive surface disposed about the optical axis. The diffractive surface has a plurality of echelettes. The echelettes in combination with the refractive power define at least one viewing diffractive order, a first additional or non-viewing diffractive order, and a second additional or non-viewing diffractive order. The at least one viewing diffractive order each has an associated viewing focus disposed along the optical axis for viewing at a distance from the eye. The non-viewing diffractive orders are distinct from the at least one viewing diffractive order. The echelettes have a profile which inhibits directing light into the first non-viewing diffractive order. The provided diffractive ophthalmic lens may be monofocal, bifocal, or multifocal.

In many embodiments, the amount of light directed to the first non-viewing diffractive order is sufficiently reduced to limit imaging degradation by light directed thereto.

In many embodiments, each echelette includes a primary zone that is a continuous function with at its connection to a secondary zone of an adjacent echelette. The profile smoothly curves along the primary and secondary zones so as to direct energy from the first non-viewing diffractive order to at least one of the at least one viewing diffractive order and/or the second non-viewing diffractive order.

In another aspect, the invention provides a diffractive ophthalmic lens for use with an eye of a person having a retina. The ophthalmic lens includes a diffractive surface with an optical axis extending therethrough. The diffractive surface has a plurality of echelettes. When viewing along the optical axis of the eye, the echelettes define at least one viewing diffractive order and a plurality of non-viewing higher diffractive orders. The at least one viewing diffractive order each has an associated viewing focus adjacent the retina for viewing at a distance from the eye. The plurality of non-viewing higher diffractive orders have foci axially separated from the retina. The echelettes also define an adjacent non-viewing diffractive order focus. This non-viewing focus is disposed closer to the retina than other non-viewing foci when viewing with the eye. The echelettes have profiles that inhibit directing viewing light energy toward the adjacent focus. The provided diffractive ophthalmic lens may be monofocal, bifocal, or multifocal.

In many embodiments, each of the higher diffractive orders is separated from the retina sufficiently to limit imaging degradation by light directed thereto. Each echelette includes a primary zone and a secondary zone extending between the optical zone and an adjacent primary zone of an adjacent echelette. The profile defined by the echelettes is essentially continuous and smoothly curve along the interfaces between the primary zones and the secondary zones so as to direct energy from the adjacent focus to the higher diffractive foci.

In another aspect, the invention provides a method for viewing with a diffractive ophthalmic lens using an eye of a person. The ophthalmic lens comprises a diffractive surface with a plurality of echelettes. The method includes the step of viewing along the optical axis of the lens with the eye at first and second viewing distances from the eye. Images are directed from the first viewing distance onto the retina using a diffractive order of the diffractive surface. Images are directed from the second viewing distance onto the retina using another diffractive order of the diffractive surface. A profile of the echelettes is selected, the profile inhibiting directing light with a non-viewing diffractive order having a focus adjacent to the retina. The diffractive ophthalmic lens may be monofocal, bifocal, or multifocal.

In many embodiments, the selected profile provides the non-viewing diffractive order with a diffraction efficiency of less than about 4 percent. In some embodiments, the selected profile provides the non-viewing diffractive order with a diffraction efficiency of less than about 2.5 percent.

In a another aspect, the invention provides a multifocal ophthalmic lens. The ophthalmic lens includes an anterior face and a posterior face. Each face has a refractive profile. The faces are disposed about an optical axis. The faces may define a clear aperture. A diffractive profile is imposed on one of the refractive profiles. The diffractive profile includes a plurality of echelettes with associated profile heights that are substantially equal to one another. The diffractive profile has, in the visible waveband, a zeroth diffractive order and a first diffractive order having a diffraction add power. The zeroth and first diffractive orders have diffraction efficiencies which change with radius from the optical axis. In other embodiments, the diffractive profile has, in the visible waveband, a first diffractive order and a second diffractive order, the difference between the diffractive orders defining a diffraction add power. The first and second diffractive orders have diffraction efficiencies which change with radius from the optical axis.

In many embodiments, the diffractive profile is characterized by a continuous function over a plurality of echelettes.

In many embodiments, the echelettes comprise a central echelette and N additional echelettes. The N additional echelettes comprise a first echelette disposed about the central echelette, a second echelette disposed about the first echelette, up to an Nth echelette disposed about an (N−1)th echelette. In some embodiments, the echelettes define zeroth and first diffractive orders having diffraction efficiencies which change with the number of surrounding echelettes. In some embodiments N is at least 4. The zeroth and the first diffractive orders have diffraction efficiencies which change depending on the number of surrounding echelettes. In other embodiments, the echelettes define first and second diffractive orders having diffraction efficiencies which change with the number of surrounding echelettes. In some such embodiments N is at least 4. The first and second diffractive orders have diffraction efficiencies which change depending on the number of surrounding echelettes.

In another aspect, the invention provides a multifocal ophthalmic lens. The ophthalmic lens includes an anterior face and a posterior face. Each face has a refractive profile. The faces are disposed about an optical axis. The faces may define a clear aperture. A diffractive profile is imposed on one of the refractive profiles. The diffractive profile includes a plurality of echelettes with associated step heights that are substantially equal to one another. The diffractive profile has, in the visible waveband, a first diffractive order and a second diffractive order having a diffraction add power. The first and second diffractive orders have diffraction efficiencies which change with radius from the optical axis.

In many embodiments, the diffractive profile is characterized by a continuous function over a plurality of echelettes.

In another aspect, the invention provides a method for viewing with a diffractive ophthalmic lens using an eye of a patient. The ophthalmic lens includes a plurality of echelettes with associated step heights that are substantially equal to one another. The echelettes each have a characteristic profile and define a diffractive surface. The diffractive surface has in the visible waveband, a zeroth diffractive order and a first diffractive order, or a first diffractive order and a second diffractive order. The method comprises changing the diffractive efficiency of the zeroth and first diffractive orders, or of the first and second diffractive orders, of the echelettes with radius from the optical axis.

In many embodiments, changing the diffractive efficiency of one or more diffractive orders of each of the echelettes with radius from the optical axis comprises changing the profile of each of the echelettes with radius from the optical axis.

In many embodiments, the echelettes comprise a central echelette and N additional echelettes. The N additional echelettes comprise a first echelette disposed about the central echelette, a second echelette disposed about the first echelette, up to an Nth echelette disposed about an (N−1)th echelette. In some embodiments, the zeroth and first diffractive orders have diffraction efficiencies which change with the number of surrounding echelettes. In some embodiments N is at least 4. The zeroth and the first diffractive orders have diffraction efficiencies which change depending on the number of surrounding echelettes.

In many embodiments, any one of the step heights do not vary by more than 20 percent from an average of all the step heights.

In another aspect of the present invention, a lens includes an anterior face with an anterior refractive profile and a posterior face with a posterior refractive profile. The faces are disposed about an optical axis and a diffractive profile is imposed on one of the refractive profiles, the diffractive profile being characterized by a continuous function over a plurality of echelettes. The plurality of echelettes comprises a central echelette and a plurality of surrounding echelettes disposed about the central echelette. At least one of the surrounding echelettes has an echelette form that is unequal to an echelette form of any of the remaining surrounding echelettes.

BRIEF DESCRIPTION OF THE DRAWINGS

FIG. 4E. is an equation for a formula for a diffractive profile according to an embodiment of the present invention.

Figure 1A:
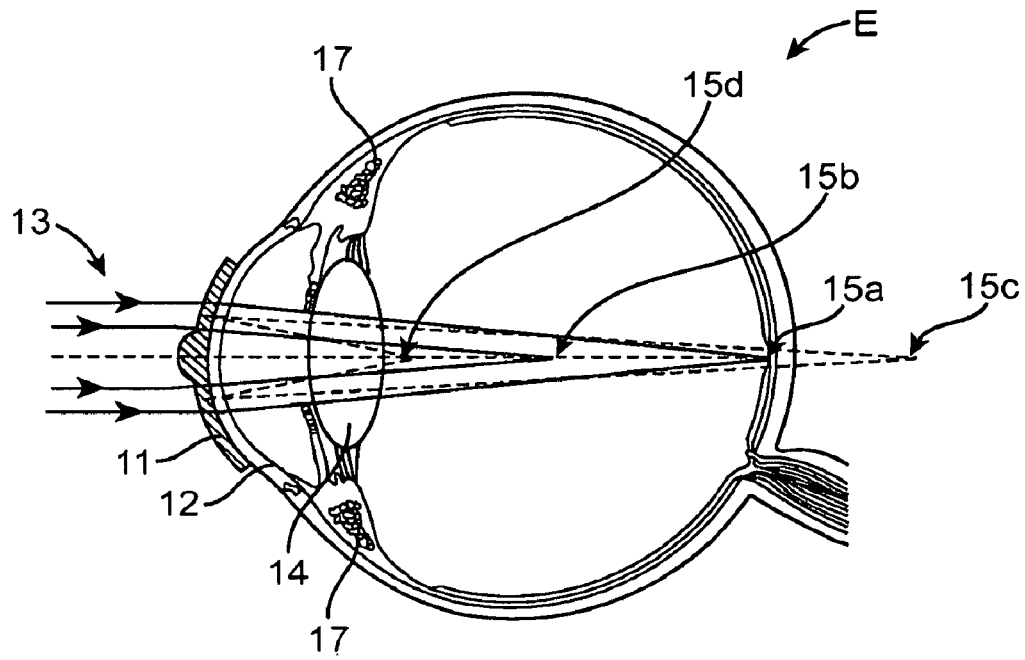
FIG. 1A is a cross-sectional view of an eye with a multifocal contact lens.

For illustration purposes, the profile geometries shown in the aforementioned figures were not drawn exactly to scale. The size of the optic is typically 5 mm or 6 mm for an IOL, but may vary between 4.5 mm and 7 mm. The heights of the diffractive profiles shown in the figures is generally in the order of about 0.5 micrometers to about 2.0 micrometers although the heights may vary depending on factors such as the amount of correction needed by the patient, the refractive index of the lens material and surrounding medium, and the desired distribution of light between wanted diffractive orders.

DETAILED DESCRIPTION OF THE INVENTION

The present invention generally provides improved lenses and imaging systems. Embodiments of the invention may find their most immediate use may be in the form of improved ophthalmic devices, systems, and methods. Exemplary embodiments of the present invention provide improved ophthalmic lenses (including, for example contact lenses, intraocular lenses (IOLs), corneal implants and the like) and associated methods for their design and use. Embodiments of the present invention include monofocal diffractive lenses, bifocal diffractive lenses, and multifocal diffractive lenses. Exemplary embodiments provide multifocal diffractive ophthalmic lenses having reduced light scatter and/or improved light energy distribution so as to enhance viewing performance, for example, through subtle shaping of a smoothly curving profile extending across a plurality of echelettes. The surface is generally optically smooth to help reduce scatter. As used herein, "optically smooth" means having an average roughness that is much smaller than the wavelength of visible light (e.g., having an rms roughness that is less that 10 nm, $\lambda/100$, or the like, where $\lambda$ is a wavelength of light) and local radii of curvatures that are larger than the wavelength of light.

Diffractive ophthalmic lenses having multiple foci often use a zero diffractive order for far vision and first diffractive order for near vision; however, other ophthalmic lenses provide multiple foci in the visible waveband using a first diffractive order for far vision and second diffractive order for near vision. Some portion of the light energy is also directed to other, non-viewing diffractive orders. As used herein, the term "viewing diffractive order" means a diffractive order of a lens or diffraction grating that is suitable for providing distant or near vision when placed within an eye. As used herein, the term "non-viewing diffractive order" means a diffractive order of a lens or diffraction grating that is not useful in forming an image on the retina of an eye from light in the visible waveband.

As used herein, the term "near vision" means vision produced by an eye that allows a subject to focus on objects that are within a range of about 25 cm to about 40 cm from the subject, or at a distance at which the subject would generally place printed material for the purpose of reading. As used herein, the terms "near vision focus" or "near focus" mean a focus produced by a lens that corresponds to near vision when the lens is placed within an eye. As used herein, the terms "distant vision" or "far vision" mean vision produced by an eye that allows a subject to focus on objects that are at a distance that is greater than or equal to 6 meters from the subject. As used herein, the terms "far vision focus" or "for focus" mean a focus produced by a lens that corresponds to far vision when the lens is placed within an eye. As used herein, the term "visible waveband" means the band of electromagnetic radiation with a wavelength in a vacuum that is between 390 nanometers and 780 nanometers.

By recognizing that foci of the non-viewing diffractive orders that are closest to a far vision focus (e.g., provided by a zeroth diffractive order or a first diffractive order) can have the larger negative effect on vision quality, and by limiting the light energy in such selected non-viewing diffractive orders, dysphotopsia (e.g., scattering or halo effects) may be mitigated, even if more total cumulative light energy ends up being directed to other non-viewing diffractive orders. A controlled shape or curvature across a plurality of echelettes can be used to tailor energies of the various foci so as to provide such benefits, and may also be used to limit deleterious scatter that can otherwise be generated by the sharp corners associated with vertical steps between adjacent conventional diffractive echelettes.

The shape or diffractive profile of a multifocal lens can impact the light energy distribution between foci. For example, known multifocal lenses often seek to distribute imaging light energy between 2 viewing foci: one (typically the zero or first diffractive order focus) corresponding with far viewing distances and one (typically the first or second diffractive order focus) corresponding to near viewing distances. The remaining light is distributed to other non-viewing foci. For example, a conventional multifocal lens with a desired even light distribution between the far and near foci "50%: 50%", may result in about 41% of the light energy directed to the far focus, about 41% of the light energy directed to the near focus, and about 18% of the light energy being directed to non-viewing and/or higher order foci, the higher order foci being generally situated symmetrically around the 2 main viewing foci. In order of diminishing brightness, the next brightest foci may, for example, be the $-1^{st}$ and $2^{nd}$ order foci, each of which are non-viewing foci and may receive about 4.5% of the light energy.

The non-viewing and/or higher order foci have a negative effect on the quality of vision. However, the negative effect of the various non-viewing foci will not be the same, and will not depend solely on the portion of incident light energy each focus receives. Instead, higher order foci that are close to the zero order focus will tend to have a disproportionately larger negative effect on perceived scatter and halo effects. Too much light energy (and thus brightness) in such higher order foci can contribute to dysphotopsia. Therefore, diffractive multifocal lenses having diffractive profiles which optimize and/or selectively tailor the light energy distribution between the various foci may improve quality of vision and reduce dysphotopsia for pseudophakic patients, contact lens users, and the like.

The structures of the present invention may also present additional advantages by enhancing the design flexibility through selectively curving echelette profiles, with the curvatures presenting additional design variables that can be used to benefit overall viewing performance. For example, varying light distributions over the diffractive profile may also provide advantages. Reading is often done in bright light conditions in which the pupil is small. In contrast, night-time driving is done in low light conditions in which the pupil is large. It may be advantageous to vary light distribution radially across the diffractive profile so that different light energy splits are provided based on the viewing situation and resulting pupil size. In some such ophthalmic lenses, a greater proportion of light energy may be transmitted to the far focus from a peripheral portion of the lens to accommodate for low light, far viewing conditions such as night time driving, with the near viewing receiving relatively more light energy from a central portion of the diffractive profile. Varying curvature and/or shapes of the echelettes radially may thus provide diffractive multifocal lenses having a diffractive profile which vary light distribution over the profile as the pupil changes in size.

As another example of the benefits of intentional and controlled curving diffractive profiles for ophthalmic lenses, the scatter of multifocal diffractive lenses may be higher than that of corresponding monofocal and/or purely refractive designs. The diffractive profile of multifocal diffractive lenses may play a significant role in producing such scatter, and appropriately controlled curving profiles may be employed to inhibit such scatter, often providing such benefits in combination with one or more of the other improvements described herein.

FIG. 1A is a cross-sectional view of an eye E fit with a multifocal contact lens 11. As shown, multifocal contact lens 11 may, for example, comprise a bifocal contact lens. Multifocal contact lens 11 covers at least a portion of cornea 12 at the front of eye E and is generally centered about the optical axis of eye E.

Each major face of lens 11, including the anterior (front) surface and posterior (back) surface, generally has a form or refractive profile. The two surfaces together, in relation to the properties of the air, tear film, cornea, and other optical components of the overall optical system, define the effects of the lens 11 on the imaging performance by eye E. Conventional, monofocal contact lenses have a refractive power based on the refractive index of the material from which the lens is made, and also on the curvature or form of the front and rear surfaces or faces of the lens.

In a young, healthy eye contraction and relaxation of ciliary muscles 17 surrounding the natural lens 14 contribute to accommodation of the eye, the process by which the eye increases optical power to maintain focus on objects as they move closer. As a person ages, the degree of accommodation decreases and presbyopia, the diminished ability to focus on near objects, often results. A patient may therefore need corrective optics having two optical powers, one for near vision and one for far vision, as provided by multifocal contact lens 11.

Multifocal lenses may make use of a variation in the refractive properties of the lens. Such lenses generally include different powers in different regions of the lens so as to mitigate the effects of presbyopia. For example, as shown in FIG. 1A, a perimeter region of refractive multifocal lens 11 may have a base power which is suitable for viewing at far viewing distances. The same refractive multifocal lens 11 may also include an inner region having a generally higher overall power (sometimes referred to as a positive add power) suitable for viewing at near distances.

As used herein the term "base power" means a power (in Diopters) of an optic or lens required to provide emmetropia. As used herein the term "base power" may additionally mean a paraxial power of an optic or lens (i.e., the power of the lens or optic for rays of collimated light impinging on the optic parallel to and near an optical axis of the optic or lens). As used herein, the term "add power" means a difference in optical power (in Diopters) between a local power of the optic or lens and the base power. When the add power is positive, the sum of the add power and the base power corresponds to a total optical power suitable for imaging an object at some finite distance from the eye onto the retina. A typical maximum add power for an optic or lens is about 3 Diopter or about 4 Diopters in the plane of the lens, although this number may be as high as 6 or more. In the case of an intraocular lens, add power of 4.0 Diopters is approximately equal to an increase in optical power of about 3 Diopters of a lens located in the spectacle plane.

Rather than relying on the refractive properties of the lens, multifocal diffractive contact lenses or IOLs have an add power or diffractive add power that is produced by a difference between two diffractive orders or powers of a diffraction grating. If the diffractive lens uses a first diffractive order to provide the add power, then the add power will generally be equal to the power of the first diffractive order. The diffractive power is conferred by a plurality of concentric diffractive zones which define a diffractive profile. The diffractive profile may either be imposed on the anterior face or posterior face or both.

The diffractive profile of a diffractive multifocal lens acts as a diffraction grating and directs incoming light into a number of diffractive orders. As light 13 enters from the front of the eye, multifocal contact lens and the natural lens 14 bend light 13 to form a far field focus 15a on retina 16 for viewing for distant objects and a near field focus 15b for objects close to the eye. Depending on the distance form the source of light 13, the focus on retina 16, the viewing focus, may be near field focus 15b instead. Far field focus 15a is often associated with a zeroth diffractive order and near field focus 15b is associated with the first diffractive order. Alternatively, in some embodiments, the far field focus 15a may be associated with a first diffractive order and near field focus 15b may be associated with the second diffractive order. Other combinations of diffractive orders are also possible for association with the far and near field foci 15a, 15b. For example, far field focus 15a may be associated with an Nth diffractive order and near field focus 15b may be associated with an (N+1)th diffractive order.

Multifocal ophthalmic lens 11 typically distributes the majority of light energy into the two viewing diffractive orders, often with the goal of splitting imaging light energy evenly (50%:50%). However, a significant portion of the incident light energy is directed into other, non-viewing diffractive orders 15c, 15d, and the like (the non-viewing diffractive orders typically comprising the $2^{nd}$, $3^{rd}$, ..., $-1^{st}$, $-2^{nd}$, $-3^{rd}$, ...) such that the $0^{th}$ and $1^{st}$ order each receive about 40.5% of the light energy when standard ideal parabolic echelettes with sharp vertical transitions are used. The remaining percentage of the light energy is received by the higher and lower orders, with the $-1$ and $2^{nd}$ order each receiving about 4.5% of the light energy for such lenses.

Figure 1B:
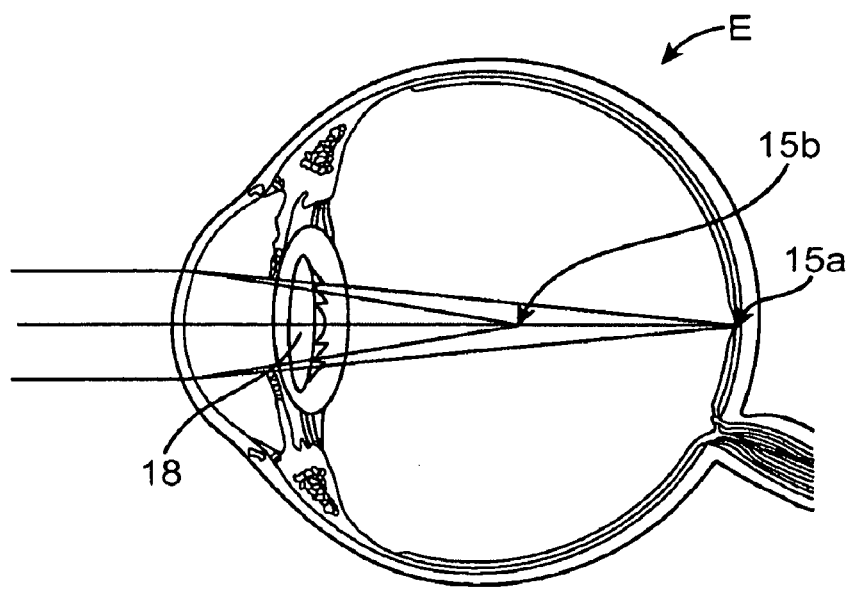
FIG. 1B is a cross-sectional view of an eye having an implanted multifocal intraocular lens.

The corrective optics may also be provided by other types of multifocal ophthalmic lenses such as multifocal intraocular lens (IOL) 18 shown in FIG. 1B. For patients with IOLs, natural lens 14 is removed and IOL 18 is placed within capsular bag 19 in eye E. IOL 18 is centered about the optical axis of the eye E. Like multifocal contact lens 11, IOL 18 often has a refractive power and a diffractive power from a number of concentric diffractive zones. Likewise, IOL 18 focuses incoming light 13 to far field focus 15a and near field focus 15b.

Figure 2A:
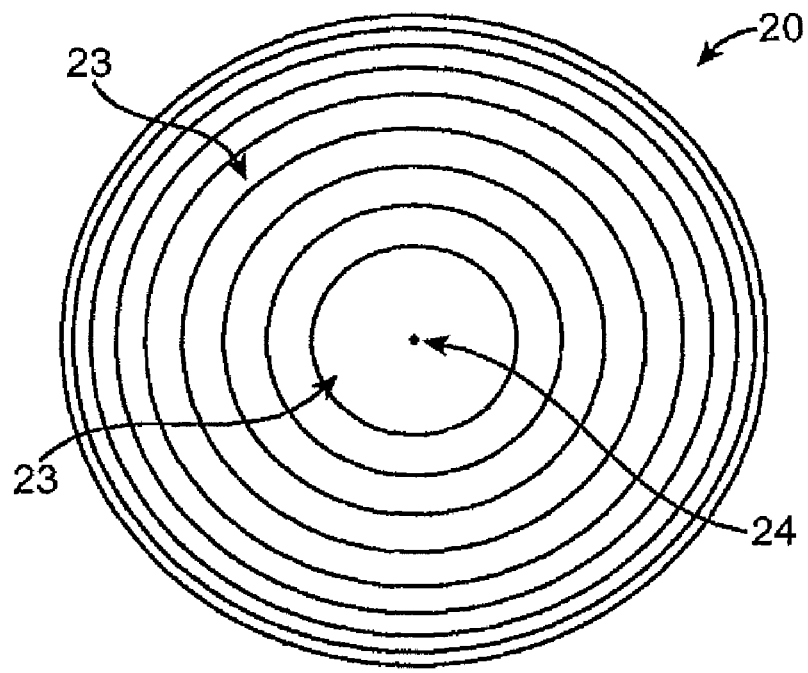
FIG. 2A is a front view of a multifocal ophthalmic lens.
Figure 2B:
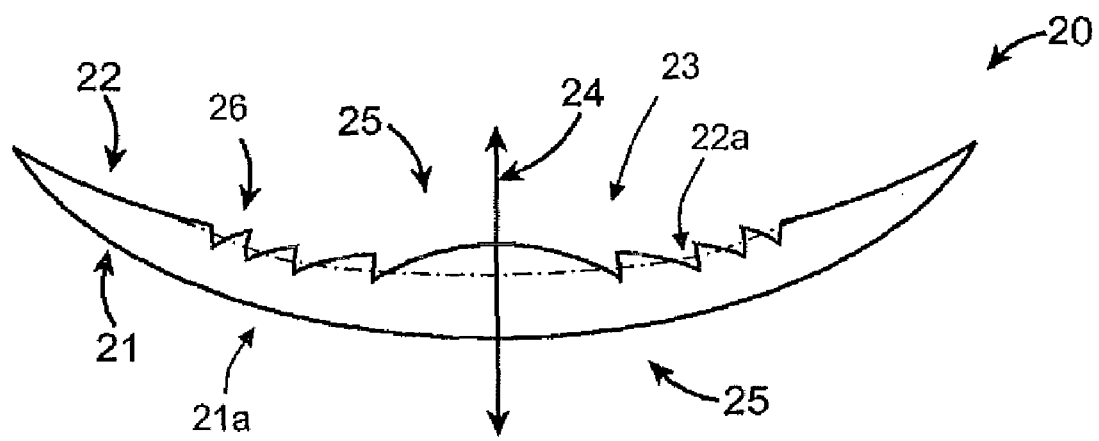
FIG. 2B is a cross-sectional view of the lens of FIG. 2A.

FIGS. 2A and 2B show a conventional or reference multifocal lens 20. Multifocal lens 20 has optical properties that may be similar to those of multifocal contact lens 11 or the multifocal IOL 18 described above. When fitted onto the eye of a subject or patient, the optical axis of lens 20 is generally aligned with an optical axis 24 of eye E. Multifocal lens 20 has an anterior lens face 21 having an anterior form or refractive profile 21a and a posterior lens face 22 having a posterior form or refractive profile 22a, the faces 21, 22 being disposed about optical axis 24. The faces 21, 22 of lens 20 typically define a clear aperture 25. As used herein, the term "clear aperture" means the opening of a lens or optic that restricts the extent of a bundle of light rays from a distant source that can imaged or focused by the lens or optic. The clear aperture is usually circular and is specified by its diameter.

The multifocal lens 20 includes a diffraction grating comprising a plurality of echelettes 26 disposed about the optical axis 24. The diffraction grating and the plurality of echelettes 24 define a conventional diffractive profile 23 that is imposed on or added to posterior refractive profile 22a. Alternatively, the diffraction grating and the plurality of echelettes 24 may define a diffractive profile 23 that is imposed on or added to anterior refractive profile 21a.

Lens 20 is in the form of a meniscus lens in the exemplary embodiment. Alternatively, lens 20 may have other forms or form factors typical of ophthalmic lenses, and the like. For example, lens 20 may have a form that is biconvex, planoconvex, plano-concave, or biconcave. The form of the lens 20 may be defined such that anterior or posterior refractive profiles 21a, 22a are spherical in shape, with each profile being characterized by a radius of curvature that is the same or different for each surface 21, 22. Alternatively, at least one of the profiles, or a portion thereof, may be an aspheric surface that is characterized by an equation with parameters for a radius of curvature, a conic constant, and/or a polynomial series (e.g., such as a Taylor series or a Zernike polynomial). Examples of such profiles or sag equations are found in U.S. Pat. Nos. 6,609,793 and 7,377,640, each of which are herein incorporated by reference in their entirety.

Figure 3A:
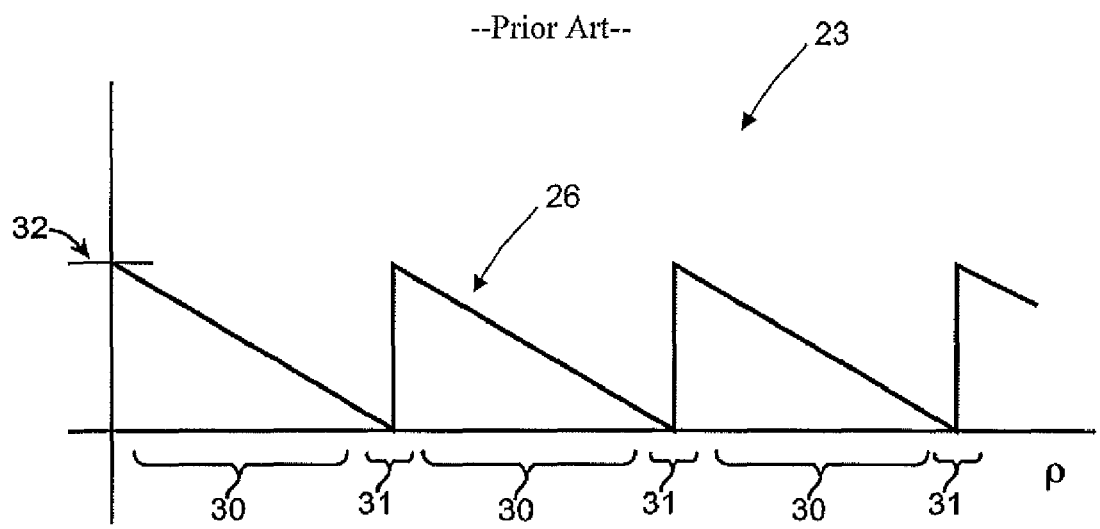
FIGS. 3A-3B are a graphical representations of a portion of the diffractive profile of a conventional multifocal lens.
Figure 3B:
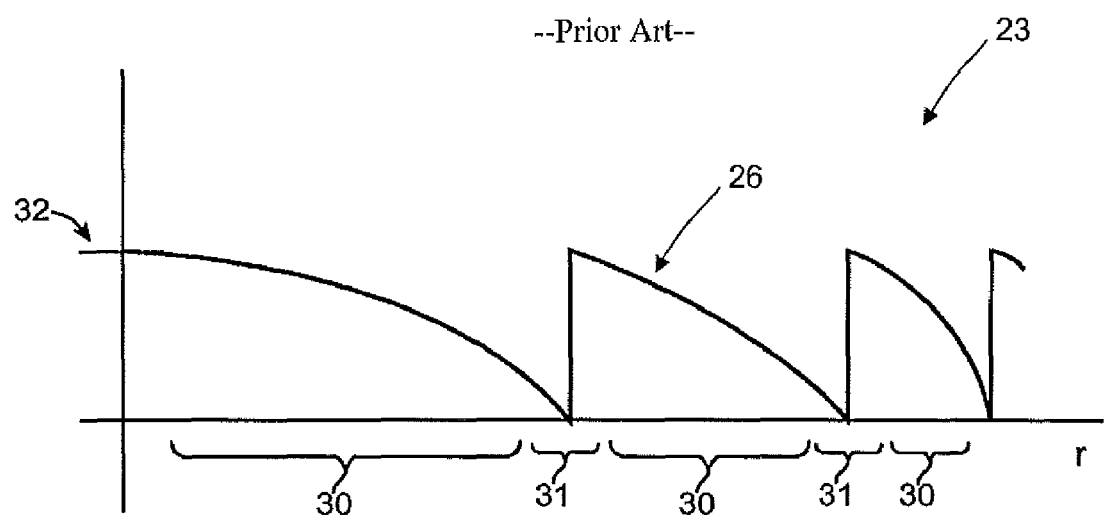

FIGS. 3A and 3B are graphical representations of a portion of the diffractive profile 23. In FIG. 3A, the displacement (from the optical axis or another reference point on a plane perpendicular to the optical axis) of each point on the echelette 26 surface is plotted against the square of the radial distance ($r^2$ or $\rho$) from the optical axis of the lens. In conventional multifocal lenses, each echelette 26 may have a diameter or distance from the optical axis which is often proportional to $\sqrt{n}$, n being the number of the echelette 26 as counted from optical axis 24. Each echelette 26 has a characteristic primary zone 30 and a step 31. Primary zone 30 has a shape or downward slope that may be linear when plotted against $\rho$ as shown in FIG. 3A. When plotted against radius r, primary zone 30 has a shape or downward slope that is parabolic as shown in FIG. 3B. The shape or slope of primary zone 30 determines the add power of lens 20.

As shown in FIGS. 3A and 3B, step 31 between adjacent echelettes is generally sharp and discontinuous. The height of the lens face sharply transitions from sloping steadily downwards to stepping vertically upwards, and abruptly back to sloping steadily downwards again. In doing so, echelettes 26 also have a characteristic echelette step or height 32 defined by the vertical distance between the lowest point and highest point of the echelette. In the case of FIGS. 3A and 3B, the echelette height 32 corresponds to a step height 32 between adjacent echelettes 26. Thus, the slope (or first derivative) and/or the curvature (second derivative) of the diffractive surface in FIGS. 3A and 3B are discontinuous at the transitions from one echelette to the next echelette.

The light energy distribution between different diffractive orders is dependent on a wavelength λ, often in the visible band, the depth of step height 32, and the difference (Δn) between the refractive index of the lens and that of the surrounding medium. For example, step height 32 having a depth of λ will distribute the majority of light energy to the $1^{st}$ order, which corresponds to the near field, and essentially be monofocal. At a depth of greater than λ/(2Δn), there will be greater light energy or intensity distributed to the $1^{st}$ order than the $0^{th}$ order, which corresponds to the far field. At a depth of less than λ/(2Δn), light energy is distributed more towards the $0^{th}$ order. Most commonly, a depth of λ/(2Δn) is used for conventional multifocal lenses. At this depth, light energy at the wavelength λ can be distributed evenly between the $1^{st}$ and $0^{th}$ orders, often at 40.5% each with the $-1^{st}$ and $2^{nd}$ orders each receiving 4.5% of the light energy.

Figure 4A:
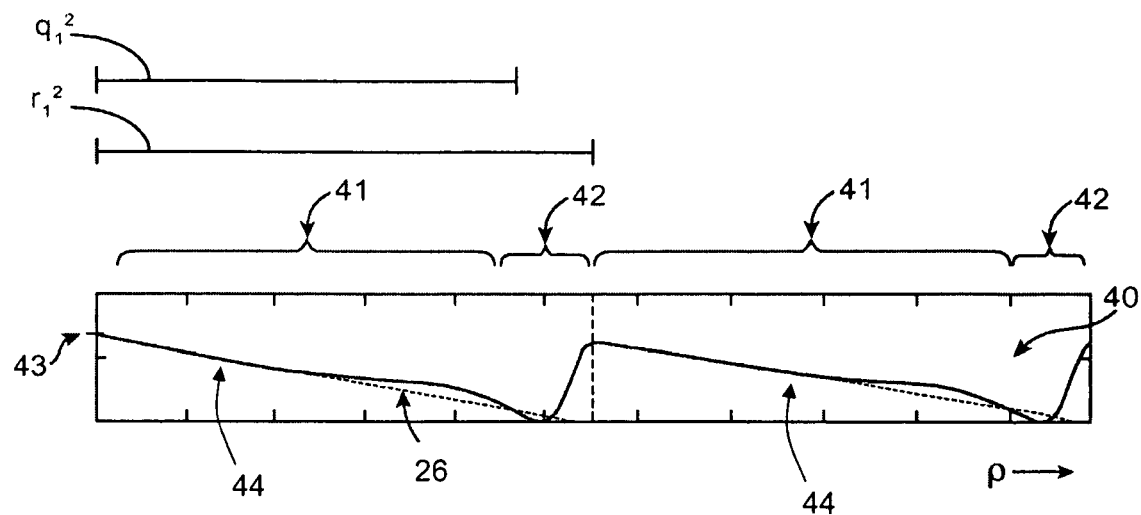
FIG. 4A is a graphical representation of a portion of the diffractive profile of a multifocal lens according to embodiments of the present invention.
Figure 4B:
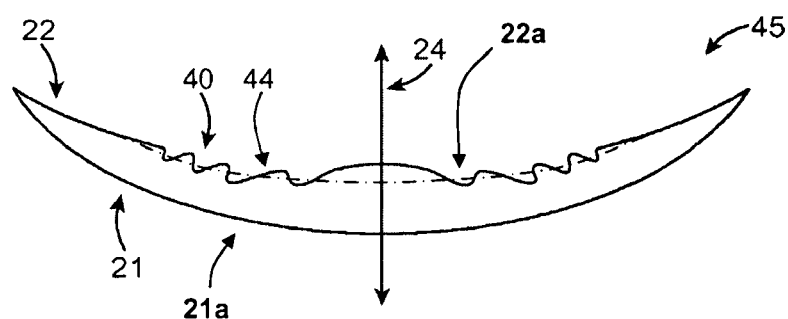
FIG. 4B is a cross-sectional view of a multifocal ophthalmic lens having the diffractive profile according to an embodiment of the present invention.

Referring to FIGS. 4A and 4B, a multifocal ophthalmic lens 45 according to an exemplary embodiment of the present invention includes a diffraction grating comprising a plurality of echelettes 44 disposed about the optical axis 24. The diffraction grating and the plurality of echelettes 44 define a diffractive profile 40 that is imposed on or added to posterior refractive profile 22a. Alternatively, the diffraction grating and the plurality of echelettes 44 define a profile 40 imposed on or added to posterior refractive profile 22a.

FIG. 4A is a graphical representation of a portion of a diffractive profile 40. The diffractive profile 40 may include a primary zone 41 and a secondary zone 42. The multifocal ophthalmic lens 45 may be generally similar to the lens 20 shown by FIGS. 2A-2B, and may have any of the lens forms or refractive profiles discussed above in relation to the lens 20. In FIG. 4A, the height of each point on the surface of echelettes 44 is plotted against the square of the radial distance ($r^2$ or $\rho$) from the optical axis of the lens. However, in contrast to diffractive profile 23 shown in FIG. 3A-3B (and represented in FIG. 4A by a dotted line), diffractive profile 40 is smooth and continuously curving. While the conventional echelette 26 has a downward slope over the entire zone, followed by a sudden or discontinuous step function, the echelette 44 and diffractive profile 40 have a continuous variation in slope over the entire primary zone 41, followed by the secondary zone 42, which joins one primary zone 41 to a proximal primary zone 41.

Apart from being continuous and free of discontinuities, the profile 40 may have any form suitable for providing diffraction characteristics according to embodiments of the present invention. In some embodiments, the diffractive profile 40 may have a first derivative and/or a second derivative in r and/or $r^2$ that is also continuous and free of any discontinuities over a predetermined radial range or over the entire clear aperture of the lens 20. The smooth, continuous profile may be configured to reduce the amount of light scattered—both by eliminating discontinuities and by reducing the energy in certain predetermined non-viewing diffractive orders. Because scatter generally occurs when light encountering an object (for example, an edge, discontinuity, or in this case, a secondary zone) that has the size of about one wavelength of the light, scatter can be reduced by having the local radii of curvature over the entire profile 40 larger than the wavelength of incoming light. The shapes of the primary and secondary zones 41, 42, as well as a characteristic echelette height 43, contribute to the light energy distribution properties of the lens.

The methods and devices described herein to reduce scatter and optimize light energy distribution are not limited in application to multifocal diffractive lenses. They may also be applicable to monofocal diffractive lenses, for example, those described in U.S. Pat. No. 6,830,332, which is herein incorporated by reference in its entirety. Monofocal diffractive lenses include a refractive portion and a monofocal diffractive portion. The diffractive portion has a single viewing focus. Implementing a smooth continuous diffractive profile having local radii of curvature greater than a design wavelength $\lambda$ would also reduce scatter. Light distribution may also be balanced between the viewing focus and non-viewing foci using the methods described.

Figure 4C:
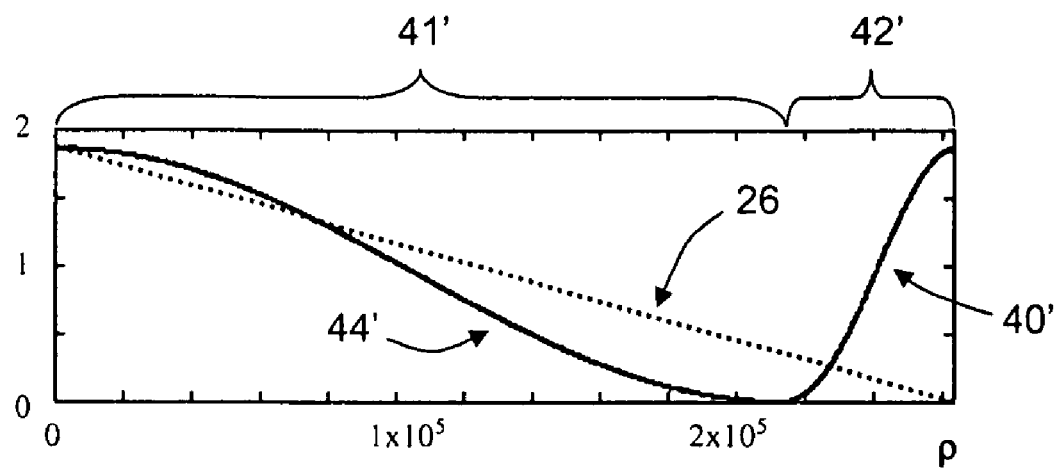
FIG. 4C is a cross-sectional view of a multifocal ophthalmic lens having the diffractive profile according to another embodiment of the present invention.

Diffractive profile 40 is plotted in FIG. 4A with a filled line. As a comparison, a conventional diffractive profile is also shown in FIG. 4A with a parabolic profile, as indicated by the dotted line. The exemplary diffractive profile 40 is defined by a single, continuous function. In some embodiments, the primary zone and the secondary zone may be defined by distinct functions that smoothly join to one another. The single, continuous function shown in FIG. 4A is a cosine function enhanced by a power function and a stretch function and is shown in FIG. 4C, where $\Delta(\rho)$ is the displacement from a reference plane perpendicular to the optical axis, in other words the height of the profile at a position $\rho$; $\rho$ is the square of a radial distance from the optical axis, en is an exponential power; $r_1$ is a radius of the first or central echelette, $q_1$ affects the size of a primary zone of each echelette, so that $r_1-q_1$ affects the size of a secondary zone of each echelette; Y_min and m are parameters influencing the shape of the echelette; Y_max is $(2q_1{}^2-r_1{}^2)/(r_1{}^2-q_1{}^2)/r_1{}^2$; X_shift is $q_1{}^2$; and $\Delta\rho$ is the height of the profile. The primary and secondary zones 41, 42 combine to provide a smooth continuous surface, generally free from discontinuities. In some embodiments, the primary zone 41 is characterized by a decreasing zone height with increasing $\rho$, while the secondary zone is characterized by increasing zone height with increasing $\rho$. The exemplary diffractive profile 40 shown in FIG. 4A is characterized by the function shown in FIG. 4C, wherein $\alpha=0.413$, en=0, r1/q1=0.9, m=1 and Y_min=$2*10^{-8}$.

Figure 4D:
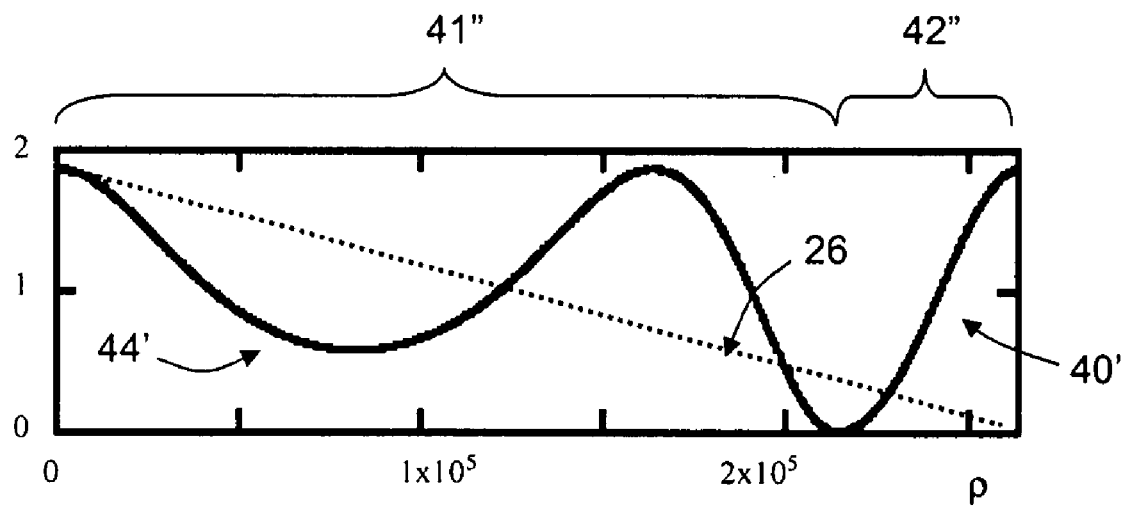
FIG. 4D is a cross-sectional view of a multifocal ophthalmic lens having the diffractive profile according to another embodiment of the present invention.

Alternatively, the lens 45 may have a diffractive profile 40' shown in FIG. 4C, which is also characterized by the equation shown in FIG. 4E, wherein $\alpha=0.413$, en=0, r1/q1=0.9, m=1 and Y_min=$2*10^{-8}$. As can be seen, the shape of each echelette 44' can be quite general. As can be seen from the profiles 40, 40', the shape of echelette 44 may be quite general. In the embodiments shown in FIGS. 4A and 4C, shape of echelette 44 is constrained only in that (1) light incident on the lens 45 has a predetermined or desired light distribution between the various diffractive orders of the lens, (2) the shape is a continuous function and (3) the local curvatures are larger than a design wavelength of light. When the light distribution is calculated, the entire profile 40 or surface of the echelette may be taken into account and treated as one optical zone. As an example of the generality possible in defining the profile 40, reference is made to FIG. 4D, where primary zone 41" includes oscillations. In general the continuity between echelettes is met by requiring the echelettes have a continuous form such that the slope and height is the same at the start and the end of each echelette, wherein the form of each echelette is described as by set of connecting continuous curves or functions, the connections being smooth by having the same slope.

In some prior art designs, the form of the echelettes is designed in order to have a maximum efficiency in the far and near viewing foci. This may lead to the well-known parabolic shape. As this shape is a discontinuous function, having a step change in height at the end of each echelette, it may pose an issue in that sharp corners are difficult to manufacture, and they can lead to light scatter. This has lead to the introduction of transitions, or transition zones, close to the outer end of the echelette. As a result, these echelettes have a main zone, being the parabolic shape of the actual theoretical design, and a secondary, or transition zone. The secondary or transition zone can be designed to minimize the optically deleterious effects of this transition zone.

One way to describe embodiments of the present invention is that the echelettes are not divided into zones or sub-zones. Under this description, the form of the total echelette is taken into account when determining the efficiency of the far and near viewing foci, or far, near and adjacent non-viewing foci. Beside the design-requirements concerning the diffractive efficiencies, the form may meet the condition of having the same height and slope at the inner point and the outer point of the echelette. As a result, the form of the echelette will be a continuous function of multiple echelettes. Also, it may deviate totally from the afore mentioned parabolic shape (e.g., profile 23).

In some embodiments, the diffractive profile 40 is divided into a primary zone 41 having a negative slope, and a secondary zone 42 having a positive slope. In some embodiments, the profile 40 includes additional zones or sub-zones. The first and second zones 41, 42, as well as any additional zones or sub-zones may all be equally important and may each be varied in order to achieve the intended lens performance (e.g., distribution of diffractive efficiencies between diffractive orders of the lens).

In addition to reducing the amount of scatter, diffractive profile 40 results in a light energy distribution to the diffractive orders as shown below in Table 1, which is different compared to a conventional, parabolic diffractive profile having the same add power (e.g., as shown by the dotted line in FIG. 4A), which distributes 81.1% of the light energy to the $0^{th}$ and $1^{st}$ orders. As seen in Table 1, the diffractive profile 40

Figure 5A:
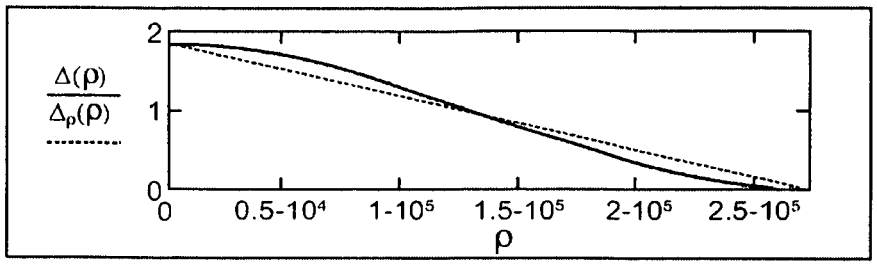
FIGS. 5A-5I show graphs of diffractive profiles of multifocal lenses according to embodiments of the present invention.
Figure 5B:
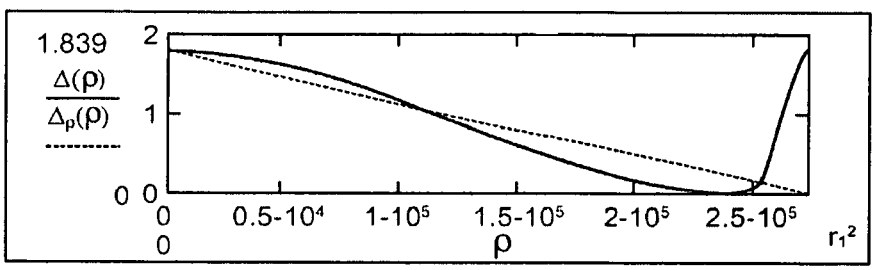
Figure 5C:
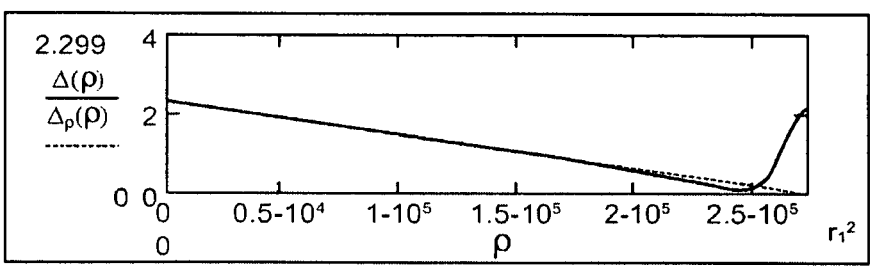
Figure 5D:
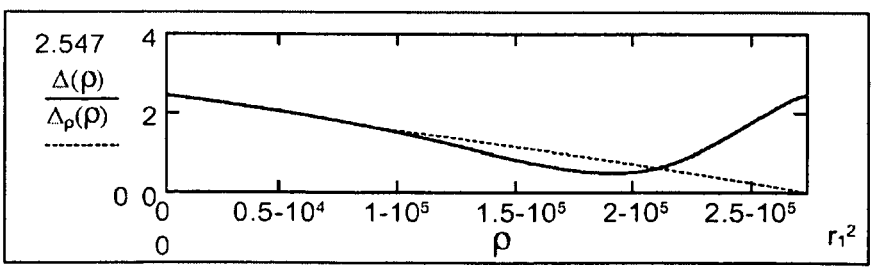
Figure 5E:
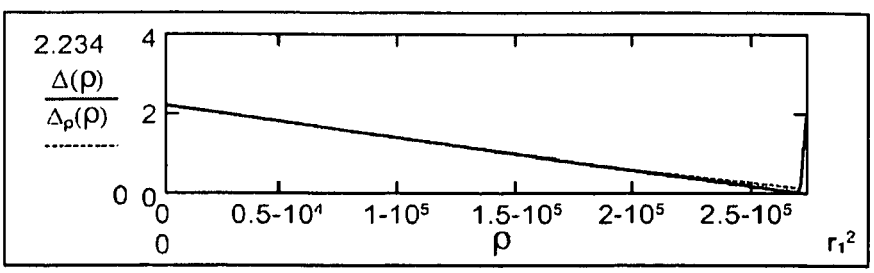
Figure 5F:
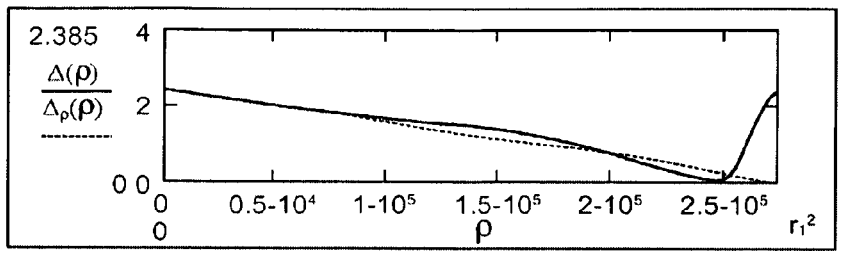
Figure 5G:
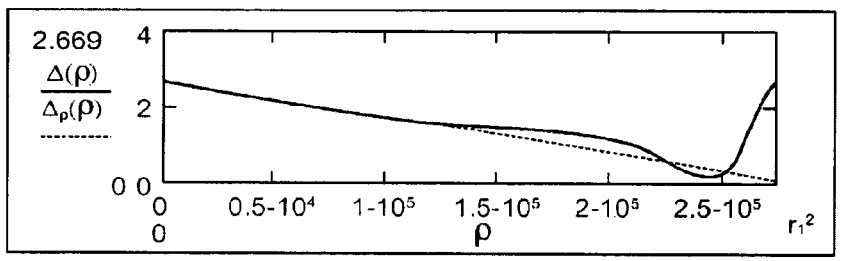
Figure 5H:
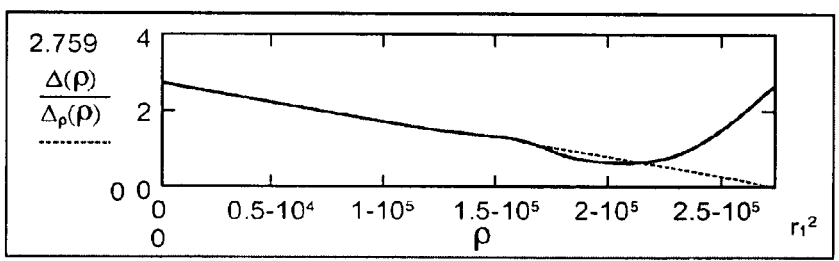
Figure 5I:
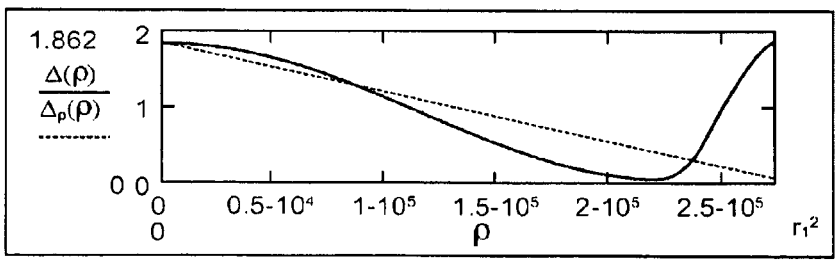

FIG. 5E shows profile code 4-3; FIG. 5F shows profile code 4-4; FIG. 5G shows profile code 4-5; FIG. 5H shows profile code 4-6; FIG. 5I shows profile code 4-7. FIGS. 5A through 5I also include the conventional diffractive profile (code 0-1 in Table 2) shown as a dotted line.

Profile 4-5 in Table 2 has a diffraction efficiency of the −1 order of 2.1%. Profile 0-1 corresponding to a conventional parabolic profile has a diffraction efficiency of the −1 order of 4.5%. Although not shown, other parameters used for function 1 may result in profiles other than profile 4-5 having a diffraction efficiency of the −1 order of less than 4.5%, preferably less than 4%, and more preferably less than 2.5%.

TABLE 2

| | Profile Code | | | | | | | | |
|---|---|---|---|---|---|---|---|---|---|
| Order | 0-1 Parabolic | 0-2 Parabolic with Cosine ending | 0-3 Parabolic with Cosine ending | 4-1 Parabolic with Cosine ending | 4-2 Parabolic with Cosine ending | 4-3 Parabolic with Cosine ending | 4-4 Parabolic with Cosine ending | 4-5 Parabolic with Cosine ending | 4-6 Parabolic with Cosine ending | 4-7 Parabolic with Cosine ending |
| −3 | 0.8% | 1.0% | 1.8% | 1.9% | 2.2% | 1.0% | 2.0% | 2.1% | 3.0% | 2.0% |
| −2 | 1.6% | 2.3% | 3.6% | 3.1% | 6.2% | 1.9% | 3.3% | 2.5% | 6.4% | 4.7% |
| −1 | 4.5% | 7.9% | 10.9% | 5.8% | 15.6% | 4.7% | 4.5% | 2.1% | 10.3% | 14.2% |
| 0 | 40.5% | 40.3% | 39.6% | 40.3% | 37.3% | 40.6% | 39.5% | 39.6% | 38.8% | 38.6% |
| 1 | 40.5% | 40.2% | 39.6% | 40.3% | 37.4% | 40.5% | 39.5% | 39.5% | 38.9% | 38.5% |
| 2 | 4.5% | 2.0% | 0.7% | 3.2% | 0.1% | 4.3% | 5.2% | 6.5% | 0.3% | 0.0% |
| 3 | 1.6% | 1.0% | 0.4% | 0.5% | 0.2% | 1.4% | 0.5% | 1.1% | 0.2% | 0.1% |
| | | | | | Parameters | | | | | |
| α | 0.5 | 0.405 | 0.408 | 0.5115 | 0.565 | 0.4955 | 0.529 | 0.592 | 0.621 | 0.413 |
| en | n/a | n/a | 0 | 4 | 2 | 10 | 2 | 3 | 5 | 0 |
| $r_1/q_1$ | n/a | n/a | 0.95 | 0.95 | 0.8 | 0.99 | 0.95 | 0.95 | 0.81 | 0.9 |
| m | n/a | n/a | 1 | 1 | 1 | 1 | 1 | 1 | 1 | 1 |
| Y_min | n/a | n/a | 0 | 2.5E−6 | 0 | 0 | 5E−06 | −2E−05 | 4E−05 | 2E−08 | distributes less overall energy—here 79.1% of the light energy—to the $0^{th}$ and 1 orders. Also, conventional diffractive profiles distributes 4.5% of the light to the $-1^{st}$ order, the non-viewing diffractive order closest to the far focus (i.e., the diffraction efficiency of the −1 order is 4.5%). In contrast, diffractive profile 40 distributes less that 4%, often being less than 3%, and preferably less that 2.5% of the incident light energy to the $-1^{st}$ order, with the exemplary embodiment delivering only 2.1% of the light energy to the $-1^{st}$ order (i.e., the diffraction efficiency of the −1 order is 2.1%). This results in less disturbance in far field vision, improving far field quality of vision and reducing dysphotopsia to a lower level.

TABLE 1

| Order | % Light Energy |
|---|---|
| −3 | 2.1% |
| −2 | 2.5% |
| −1 | 2.1% |
| 0 | 39.6% |
| 1 | 39.5% |
| 2 | 6.5% |
| 3 | 1.1% |

Figure 6A:
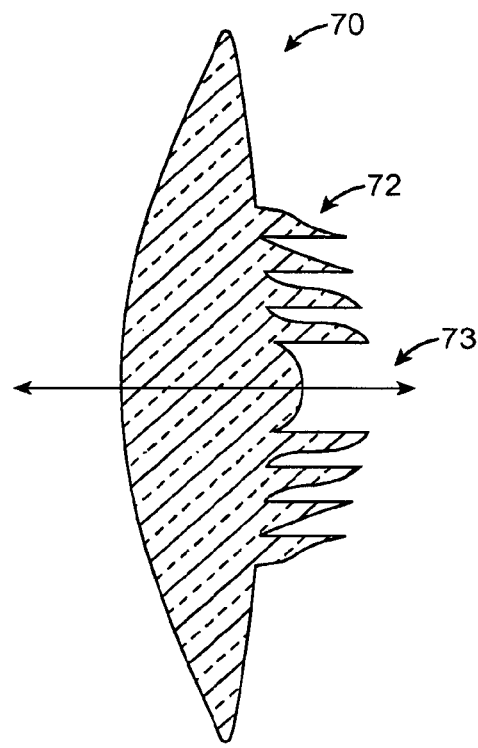
FIG. 6A is a cross-sectional view of a multifocal lens according to embodiments of the present invention having constant echelette height of the secondary zones and varying shapes of the primary zones with radius.
Figure 6B:
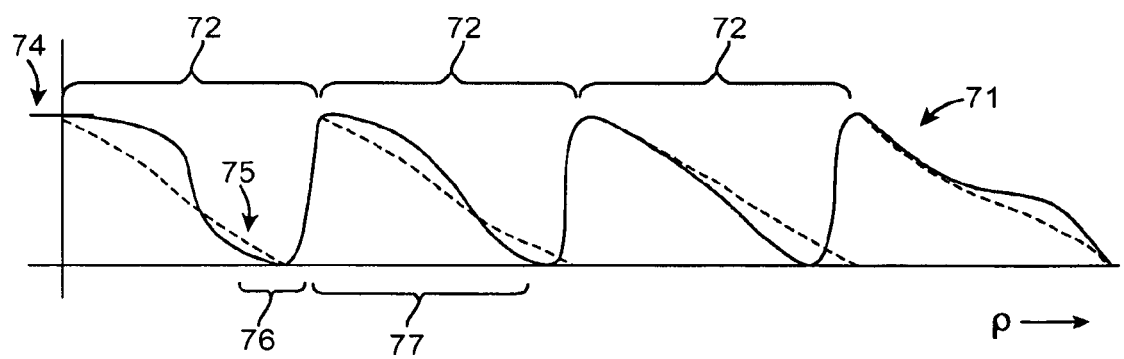
FIG. 6B is a graphical representation of the diffractive profile of the lens of FIG. 7A.
Figure 7A:
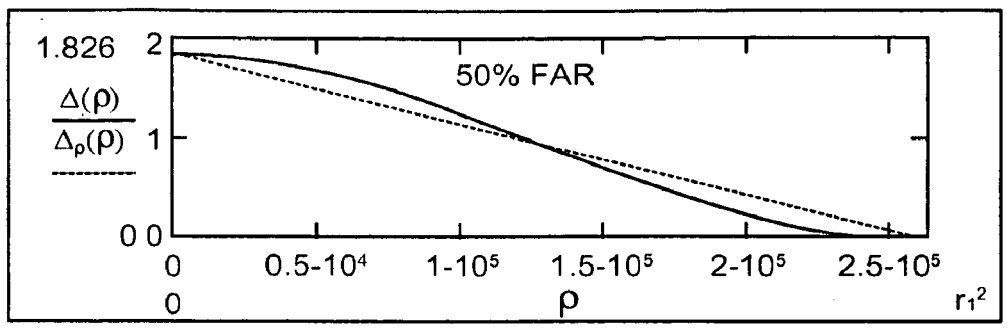
FIGS. 7A-7D show graphs of the diffractive profiles of individual echelettes according to embodiments of the present invention.
Figure 7B:
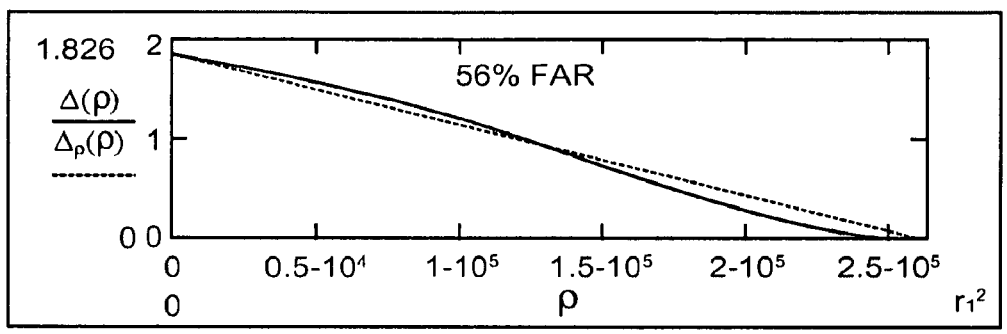
Figure 7C:
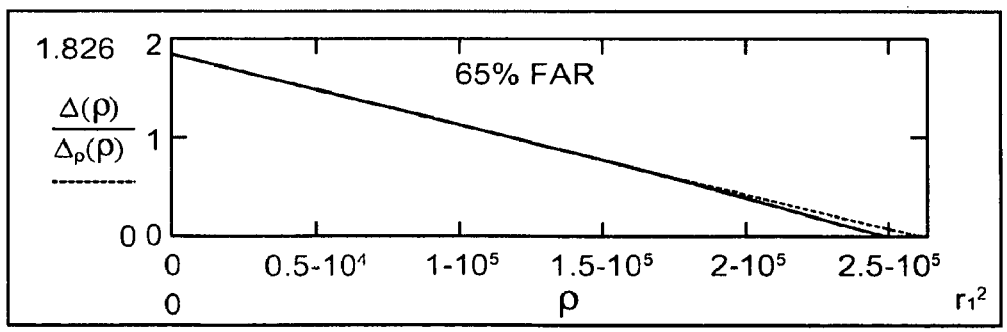
Figure 7D:
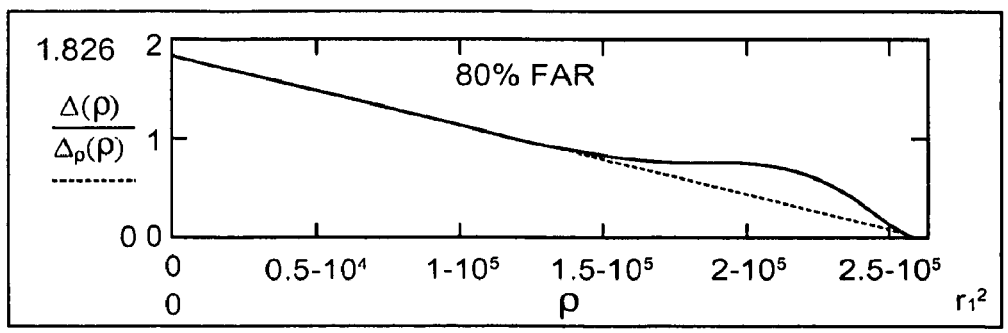

FIGS. 5A through 5I shows graphs of diffractive profiles according to the equation shown in FIG. 4E computed with the parameters shown below in Table 2. Table 2 shows the light distribution per diffractive order for the various diffractive profiles shown by FIGS. 5A-5I. FIG. 5A shows profile code 0-2 from the table, FIG. 5B shows profile code 0-3, FIG. 5C shows profile code 4-1; FIG. 5D shows profile code 4-2;

FIG. 6A shows a cross-sectional view of an alternative multifocal ophthalmic lens 70. Like previously described multifocal, ophthalmic lenses, lens 70 comprises a diffraction grating including a number of echelettes 72 spaced about optical axis 73. Echelettes 72 of lens 70 each share a common echelette height 74. However, as seen in FIG. 6B, each echelette 72 has a different shape in $r^2$, which changes the diffractive efficiency of each echelette. Hence, lens 70 may provide pupil-dependent variable imaging energy distribution similar to that provided by variable step height apodization (e.g., as described in U.S. Pat. No. 5,699,142 in the name of Lee et al.), but without progressive variations in echelette or step height. As a comparison, a conventional diffractive profile is also shown in FIG. 6A with a parabolic profile, as indicated by the dotted line.

FIG. 6B is a graphical representation of the diffractive profile 71 of lens 70, plotting the height of diffraction grating at a particular point of echelette 72 versus ρ, the square of the radius or distance displaced from the optical axis, and shown with a conventional diffractive profile 75, shown by the dotted line. FIG. 7A-7D show graphs of the diffractive profiles of individual echelettes and the diffraction efficiency in the far focus order. Echelettes 72 can be defined by the equation shown in FIG. 4E, but each using a different set of parameters. FIGS. 7A, 7B, 7C and 7D show the diffractive profiles of an echelettes having a diffractive efficiency of approximately 50%, 56%, 65% and 80%, respectively, in the far focus (relative to the near focus). Table 3A below shows a number of echelettes 72 each having a different diffractive efficiency depending on the parameters used for the equation shown in FIG. 4E. Table 3B shows the parameters used and the resulting diffraction efficiency for the far focus as well as the percentage of light energy lost to higher order, non-viewing foci.

TABLE 3A

| Echelette | % FAR | Focus Order -3 | -2 | -1 | 0 | 1 | 2 | 3 |
|---|---|---|---|---|---|---|---|---|
| 1 | 50% | 1.0% | 2.3% | 7.9% | 40.2% | 40.2% | 2.0% | 1.1% |
| 2 | 52% | 1.0% | 2.3% | 7.8% | 41.6% | 39.0% | 2.1% | 1.1% |
| 3 | 53% | 1.0% | 2.2% | 7.8% | 43.0% | 37.8% | 2.2% | 1.1% |
| 4 | 54% | 1.0% | 2.1% | 7.4% | 44.0% | 36.9% | 2.3% | 1.1% |
| 5 | 56% | 0.9% | 2.1% | 7.1% | 45.4% | 35.7% | 2.4% | 1.1% |
| 6 | 57% | 0.9% | 2.0% | 6.9% | 46.6% | 34.6% | 2.6% | 1.2% |
| 7 | 59% | 0.9% | 1.9% | 6.5% | 48.0% | 33.4% | 2.8% | 1.2% |
| 8 | 61% | 0.9% | 1.9% | 6.1% | 49.4% | 32.2% | 3.1% | 1.2% |
| 9 | 62% | 0.9% | 1.9% | 5.6% | 50.8% | 31.0% | 3.4% | 1.2% |
| 10 | 63% | 0.9% | 1.9% | 5.2% | 52.0% | 29.9% | 3.6% | 1.3% |
| 11 | 65% | 0.9% | 1.8% | 4.8% | 53.4% | 28.7% | 3.8% | 1.3% |
| 12 | 69% | 0.9% | 1.6% | 4.1% | 56.5% | 25.9% | 4.2% | 1.5% |
| 13 | 73% | 0.8% | 1.4% | 3.4% | 60.2% | 22.6% | 4.5% | 1.7% |
| 14 | 76% | 0.8% | 1.1% | 2.9% | 63.4% | 19.7% | 4.6% | 2.0% |
| 15 | 80% | 0.7% | 0.8% | 2.7% | 66.8% | 16.6% | 4.3% | 2.2% |
| 32 | 80% | 0.7% | 0.8% | 2.7% | 66.8% | 16.6% | 4.3% | 2.2% |

TABLE 3B

| Echelette | α | en | $r_1/q_1$ | m | Y_min | % Far | Loss |
|---|---|---|---|---|---|---|---|
| 1 | 0.4075 | 0 | 0.9999 | 10 | 0.0000001 | 50% | 20% |
| 2 | 0.4075 | 0.09 | 0.9999 | 10 | 0.0000001 | 51.6% | 19% |
| 3 | 0.4075 | 0.2 | 0.9999 | 10 | 0.0000001 | 53.2% | 19% |
| 4 | 0.4075 | 0.3 | 0.9999 | 10 | 0.0000001 | 54.4% | 19% |
| 5 | 0.4075 | 0.46 | 0.9999 | 10 | 0.0000001 | 56.0% | 19% |
| 6 | 0.4075 | 0.63 | 0.9999 | 10 | 0.0000001 | 57.4% | 19% |
| 7 | 0.4075 | 0.9 | 0.9999 | 10 | 0.0000001 | 58.9% | 19% |
| 8 | 0.4075 | 1.3 | 0.9999 | 10 | 0.0000001 | 60.5% | 18% |
| 9 | 0.4075 | 2 | 0.9999 | 10 | 0.0000001 | 62.1% | 18% |
| 10 | 0.4075 | 3 | 0.9999 | 10 | 0.0000001 | 63.5% | 18% |
| 11 | 0.4075 | 5 | 0.9999 | 10 | 0.0000001 | 65.0% | 18% |
| 12 | 0.4075 | 5 | 0.9999 | 10 | 0.000003 | 68.5% | 18% |
| 13 | 0.4075 | 5 | 0.9999 | 10 | 0.000006 | 72.7% | 17% |
| 14 | 0.4075 | 5 | 0.9999 | 10 | 0.0000036 | 76.3% | 17% |
| 15 | 0.4075 | 5 | 0.9999 | 10 | 0.0000118 | 80% | 17% |
| 32 | 0.4075 | 5 | 0.9999 | 10 | 0.0000118 | 80% | 17% |

As seen from Tables 3A and 3B, by gradually varying the shape of each echelette as a function of distance or radius from the optical axis, the diffraction efficiency for the $0^{th}$ order or far focus is gradually increased from 50% to 80%.

The results from Tables 3A and 3B are exemplary of the benefits provided by a multifocal lens, such as the multifocal lens 70, in which at least one echelette surrounding a central echelette has an echelette form that is different from the echelette form of the remaining echelettes surrounding the central echelette. As used herein, the term "echelette form" means the shape of the profile of the echelette when plotted verses radius squared ($r^2$ or ρ) from the optical axis of an optic containing the echelette. Two echelettes are considered to have the same echelette form if profiles of each verses radius squared is the same when normalized to the echelette height. For example, each of the echelettes of a prior art apodized diffraction grating would be considered to generally have the same echelette forms. By contrast, the echelettes in FIGS. 5A-5I or Tables 3B are examples of echelettes having echelette forms that are not equal to one another, since the form of any one of these echelettes could not be made equal to the others by a simple linear scaling constant.

In some embodiments, a diffractive lens is made of a gradient index material having a refractive index that changes with increasing radius from the optical axis (e.g., the lens may have a refractive index that decrease with increasing radius from the optical axis). In any such embodiments, the refractive index change effectively changes the optical path length of the lens with increasing radius from the optical axis. Such a lens material may be used with any of the lenses or profiles discussed above herein to provide an additional design parameter for controlling the optical performance (e.g., the diffraction efficiencies of various diffractive orders) of a diffractive lens. Examples of the use of gradient materials in ophthalmic lenses is discussed in the article titled "Radial gradient index intraocular lens: a theoretical model" (Damian Siedlecki, et al., Journal of Modern Optics, Vol. 55, Nos. 4-5, 20 Feb.-10 Mar. 2008, 639-647), which is herein incorporated by reference in its entirety. For example, such a material could be used with the lenses discussed and shown in FIGS. 2A, 3A, 4A-4D, 5A-5I, 6A, 7A-7D. In some embodiments, the gradient index material is used with an otherwise conventional diffractive lens. In some embodiments, the step height or echelette height is varied in combination with the gradient index to adjust the energy going into specific diffraction orders of the lens or to change the diffraction efficiency of the echelettes or the overall diffraction efficiency of the lens with increasing radius from the optical axis of the lens. In addition, the lens material and the diffractive profile may be configured so that the diffractive lens has a negative spherical aberration or some other aberration, for example, to correct for a positive spherical aberration or some other aberration of a surface of the lens and/or of a cornea into which the lens is placed or inserted.

Figure 8A:
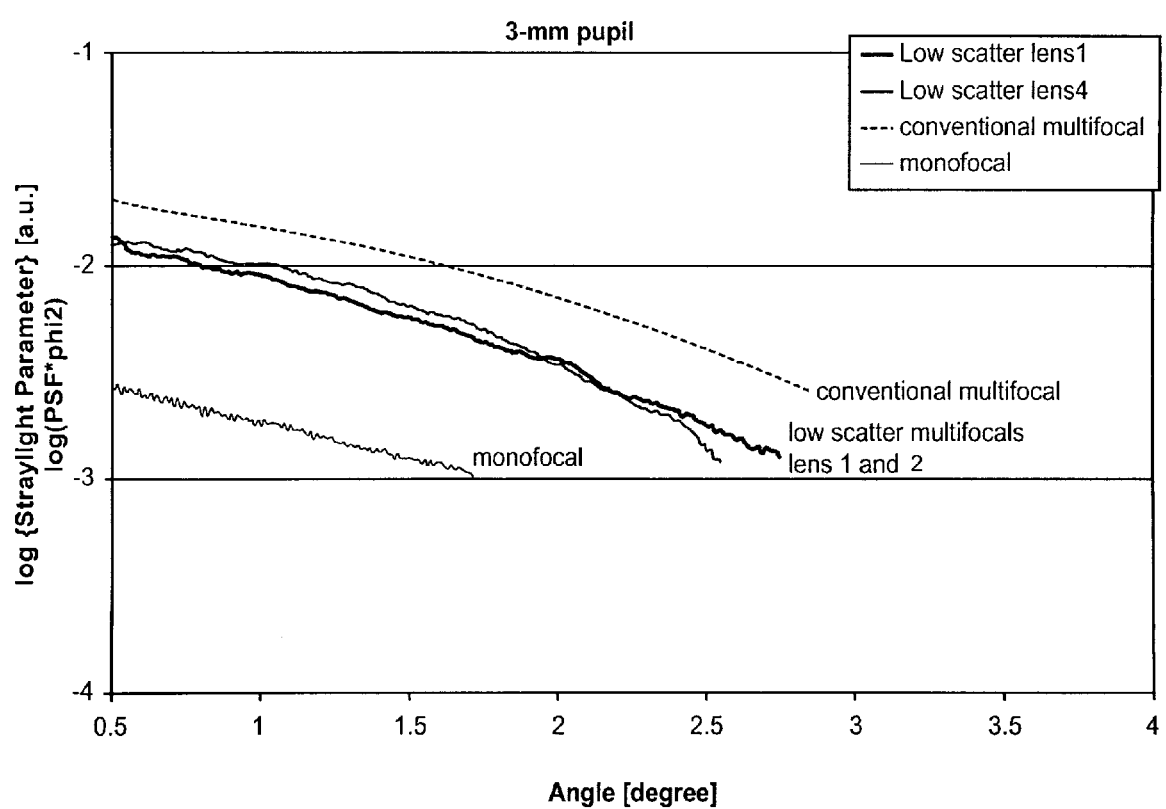
FIGS. 8A-8B show graphs of the light scattering characteristics of lenses of the present invention versus other multifocal and monofocal lenses.

Experiment A:

The light scatter characteristics of two sample multifocal lenses according to the present invention were measured and compared to that of a comparable monofocal lens and a comparable multifocal lens with a conventional diffractive profile. The conventional monofocal and multifocal lenses are generally similar except that the conventional monofocal lens has a continuous surface without a diffraction profile and a lower surface roughness. Apart from new diffractive profiles defined by a single, continuous function as previously described, the two sample multifocal lenses are identical to the conventional lenses. For instance, the sample lenses and the conventional multifocal lenses have the same light distribution (50%:50%) between the far and near foci. The amount of scatter was measured for each of the lenses using an eye model and a bright white light source, resulting in the graph shown in FIG. 8A. The vertical axis in FIGS. 8A and 8B tracks a stray light parameter, which represents the amount of scatter. The stray light parameter is given in a logarithmic scale and is defined in the reference, van den Berg, T. J., 1995, Optom. Vis. Sci., 72(2), 52-9, which is herein incorporated in its entirety. The light scatter test reveals a lower amount of light scatter from the two exemplary multifocal lenses.

Figure 8B:
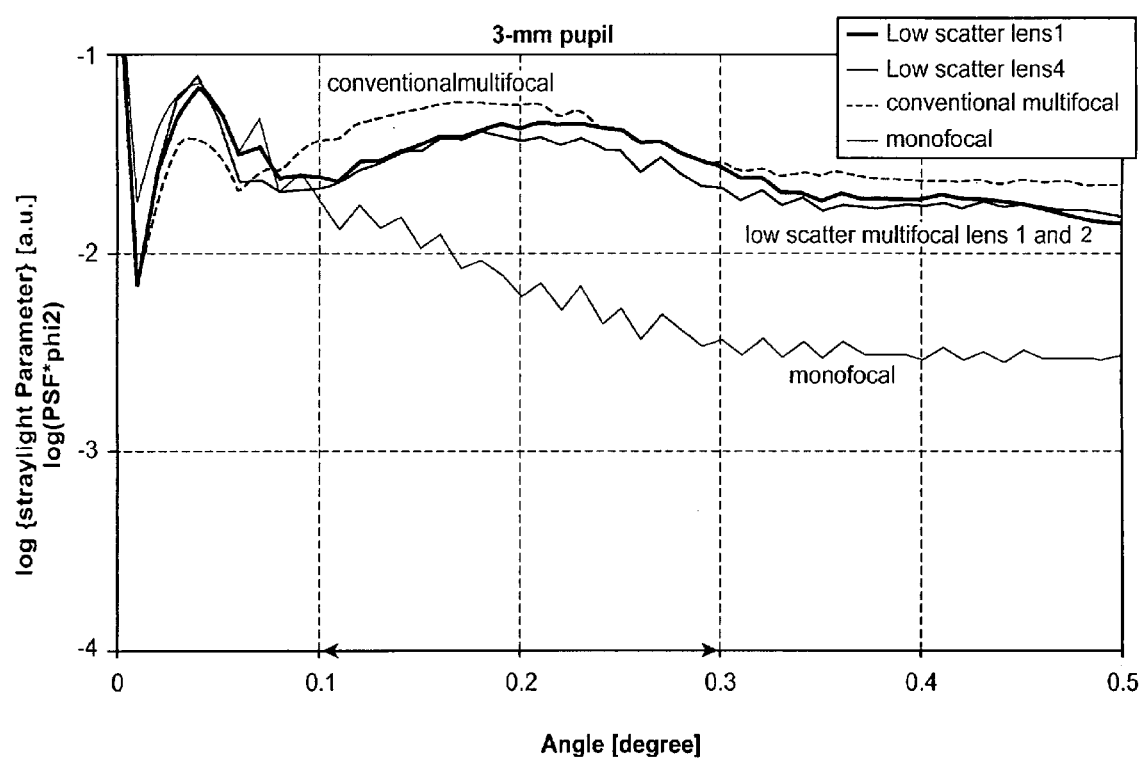

As shown in FIG. 8B, the tests also revealed a lower intensity of the primary halo. The stray light up to 0.3 degrees is attributed to the primary halo, which originates from the $1^{st}$ and $-1^{st}$ order foci. The intensity in the area of 0.1 to 0.3 degrees of the two exemplary multifocal lenses was slightly lower than that of the conventional multifocal lens.

The embodiments described above, including accompanying drawings, figures, functions and tables, are for illustrative purposes to explain aspects of the present invention. Those skilled in the art will recognize that changes and modifications can be made without departing from the scope of the invention, which is solely limited by the claims as follows.

What is claimed is:

1. A multifocal ophthalmic lens, comprising:
   an anterior face with an anterior refractive profile and a posterior face with a posterior refractive profile, the faces disposed about an optical axis;
   a diffractive profile imposed on one of the refractive profiles, the diffractive profile characterized by a continuous function over a plurality of echelettes and having, in the visible waveband, a zeroth diffractive order associated with a far focus, a first diffractive order associated with an add power of the lens, and a minus one diffractive order associated with a non-viewing diffractive order closest to the far focus; wherein
   the minus one diffractive order has a lower diffraction efficiency than a reference lens having the same refractive profiles and add power, the reference lens having a diffractive profile that is parabolic.

2. The multifocal ophthalmic lens of claim 1, wherein the diffraction efficiency of the minus one diffractive order is less than about 4 percent.

3. The multifocal ophthalmic lens of claim 1, wherein the diffraction efficiency of the minus one diffractive order is less than 2.5 percent.

4. The multifocal ophthalmic lens of claim 1, wherein the diffractive profile is characterized by a continuous function over a plurality of echelettes, the continuous function defined by the relationship:

$$\Delta(\rho) := \Delta_0 \cdot \left[\left[1 - \left(\frac{\rho}{r_1^2}\right)^{en}\right] \cdot \left[1 - \left(\frac{\rho}{r_1^2}\right)\right] + \left[\left(\left(\frac{\rho}{r_1^2}\right)\right)^{en}\right] \cdot \left[0.5 + 0.5 \cdot \cos\left[\pi \cdot \frac{\rho}{q_1^2} \cdot \left[1.0 + (\rho - q_1^2) \cdot \left[Y\_min + (Y\_max - Y\_min) \cdot \left[0.5 \cdot \tanh\left[\frac{(\rho - X\_shift)}{m}\right] + 0.5\right]\right]\right]\right]\right]\right]$$

where $\rho$ is the square of a radius from the optical axis, en is an exponential power; $r_1$ is a radius of the first or central echelette, $q_1$ affects a size of a primary zone of each echelette, $r_1 - q_1$ affects a size of a secondary zone of each echelette; Y_min and m are parameters influencing the shape of the echelette; Y_max is equal to $(2q_1^2 - r_1^2)/(r_1^2 - q_1^2)/r_1^2$; X_shift is equal to $q_1^2$; and $\Delta\rho$ is a height of the profile.

* * * * *